(12) United States Patent
Hoarau et al.

(10) Patent No.: US 8,961,504 B2
(45) Date of Patent: Feb. 24, 2015

(54) OPTICAL HYDROLOGY ARRAYS AND SYSTEM AND METHOD FOR MONITORING WATER DISPLACEMENT DURING TREATMENT OF PATIENT TISSUE

(75) Inventors: Carine Hoarau, Lafayette, CA (US); Ronald J. Podhajsky, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1055 days.

(21) Appl. No.: 12/757,340

(22) Filed: Apr. 9, 2010

(65) Prior Publication Data
US 2011/0251605 A1 Oct. 13, 2011

(51) Int. Cl.
| A61B 18/00 | (2006.01) |
| A61B 5/00  | (2006.01) |
| A61B 18/12 | (2006.01) |
| A61B 18/14 | (2006.01) |

(52) U.S. Cl.
CPC ........... *A61B 5/4875* (2013.01); *A61B 18/1233* (2013.01); *A61B 5/0075* (2013.01); *A61B 5/0084* (2013.01); *A61B 18/12* (2013.01); *A61B 18/1445* (2013.01); *A61B 18/1477* (2013.01); *A61B 2018/0063* (2013.01)
USPC .......................................................... 606/34

(58) Field of Classification Search
USPC ............................................... 606/27, 34, 41
See application file for complete search history.

(56) References Cited

U.S. PATENT DOCUMENTS

| D263,020 S | 2/1982 | Rau, III |
| D295,893 S | 5/1988 | Sharkany et al. |
| D295,894 S | 5/1988 | Sharkany et al. |
| 4,760,845 A * | 8/1988 | Kovalcheck ................. 606/28 |
| D348,930 S | 7/1994 | Olson |
| 5,383,880 A | 1/1995 | Hooven |
| 5,389,098 A | 2/1995 | Tsuruta et al. |
| 5,586,982 A * | 12/1996 | Abela ......................... 606/28 |

(Continued)

FOREIGN PATENT DOCUMENTS

| DE | 2415263 | 10/1975 |
| DE | 2514501 | 10/1976 |

(Continued)

OTHER PUBLICATIONS

U.S. Appl. No. 09/387,883, filed Sep. 1, 1999.

(Continued)

*Primary Examiner* — Michael Peffley
*Assistant Examiner* — Daniel Fowler

(57) ABSTRACT

A system that monitors water displacement in tissue during patient therapy includes a generator supplying electrosurgical energy to tissue, a spectrometer operably coupled to the generator, and a processor communicating with the generator and with the spectrometer having a light source for exposing tissue to light and a light sensor. The light sensor is configured to sense changes in light through tissue in response to tissue treatment and communicate the changes to the processor to determine tissue hydration levels and motility. A plurality of optical fibers may be configured in an array to communicate light between the generator and tissue. An optical temperature monitor may communicate with the processor and be coupled to an optical fiber. The optical fibers may have an optic fiber distance between adjacent optical fibers. The system may be incorporated within an electrosurgical pencil or a forceps. A corresponding method of detecting hydration is also disclosed.

13 Claims, 18 Drawing Sheets

(56) References Cited

U.S. PATENT DOCUMENTS

| | | | |
|---|---|---|---|
| D384,413 S | 9/1997 | Zlock et al. | |
| 5,762,609 A | 6/1998 | Benaron et al. | |
| D424,694 S | 5/2000 | Tetzlaff et al. | |
| D425,201 S | 5/2000 | Tetzlaff et al. | |
| 6,175,768 B1* | 1/2001 | Arndt et al. | 607/101 |
| D449,886 S | 10/2001 | Tetzlaff et al. | |
| D457,958 S | 5/2002 | Dycus et al. | |
| D457,959 S | 5/2002 | Tetzlaff et al. | |
| 6,537,209 B1 | 3/2003 | Pinkhasik et al. | |
| D493,888 S | 8/2004 | Reschke | |
| D496,997 S | 10/2004 | Dycus et al. | |
| D499,181 S | 11/2004 | Dycus et al. | |
| 6,869,430 B2* | 3/2005 | Balbierz et al. | 606/41 |
| D509,297 S | 9/2005 | Wells | |
| 7,011,657 B2 | 3/2006 | Truckai et al. | |
| D525,361 S | 7/2006 | Hushka | |
| D531,311 S | 10/2006 | Guerra et al. | |
| 7,137,980 B2 | 11/2006 | Buysse et al. | |
| D533,942 S | 12/2006 | Kerr et al. | |
| D535,027 S | 1/2007 | James et al. | |
| 7,160,299 B2 | 1/2007 | Baily | |
| D541,418 S | 4/2007 | Schechter et al. | |
| D541,938 S | 5/2007 | Kerr et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,655,007 B2 | 2/2010 | Baily | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 7,749,217 B2 | 7/2010 | Podhajsky | |
| 2003/0069571 A1 | 4/2003 | Treat et al. | |
| 2003/0171747 A1 | 9/2003 | Kanechira et al. | |
| 2004/0030332 A1 | 2/2004 | Knowlton et al. | |
| 2004/0078035 A1 | 4/2004 | Kanchira et al. | |
| 2004/0210282 A1 | 10/2004 | Flock et al. | |
| 2004/0240281 A1 | 12/2004 | Kim | |
| 2005/0004564 A1 | 1/2005 | Wham et al. | |
| 2005/0033278 A1 | 2/2005 | McClurken et al. | |
| 2005/0059858 A1 | 3/2005 | Frith et al. | |
| 2005/0131390 A1 | 6/2005 | Heinrich et al. | |
| 2005/0203504 A1 | 9/2005 | Wham et al. | |
| 2006/0089637 A1* | 4/2006 | Werneth et al. | 606/41 |
| 2006/0116675 A1 | 6/2006 | McClurken et al. | |
| 2007/0016182 A1 | 1/2007 | Lipson et al. | |
| 2007/0060919 A1 | 3/2007 | Isaacson et al. | |
| 2007/0078456 A1 | 4/2007 | Dumbauld et al. | |
| 2007/0106297 A1 | 5/2007 | Dumbauld et al. | |
| 2007/0156140 A1 | 7/2007 | Baily | |
| 2007/0173811 A1 | 7/2007 | Couture et al. | |
| 2007/0270792 A1* | 11/2007 | Hennemann et al. | 606/41 |
| 2007/0287998 A1* | 12/2007 | Sharareh et al. | 606/41 |
| 2008/0009860 A1 | 1/2008 | Odom | |
| 2008/0039836 A1 | 2/2008 | Odom et al. | |
| 2008/0319442 A1 | 12/2008 | Unger et al. | |
| 2009/0157071 A1 | 6/2009 | Wham et al. | |
| 2009/0157072 A1 | 6/2009 | Wham et al. | |
| 2009/0157075 A1 | 6/2009 | Wham et al. | |
| 2009/0204114 A1 | 8/2009 | Odom et al. | |
| 2009/0261804 A1 | 10/2009 | McKenna et al. | |
| 2010/0049187 A1* | 2/2010 | Carlton et al. | 606/34 |
| 2010/0076431 A1 | 3/2010 | Allen, IV | |
| 2010/0076432 A1 | 3/2010 | Horner | |
| 2010/0087816 A1 | 4/2010 | Roy | |
| 2010/0094271 A1 | 4/2010 | Ward et al. | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009317 | 10/2007 |
| DE | 19738457 | 1/2009 |
| EP | 1159926 | 12/2001 |
| EP | 1472984 | 11/2004 |
| EP | 1201195 | 2/2006 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/01847 | 1/2001 |
| WO | WO 01/54604 | 8/2001 |
| WO | WO 02/067798 | 9/2002 |
| WO | WO 03/090630 | 11/2003 |
| WO | WO 2004/073753 | 9/2004 |
| WO | WO 2005/110264 | 11/2005 |
| WO | WO 2008/112147 | 9/2008 |

OTHER PUBLICATIONS

U.S. Appl. No. 09/591,328, filed Jun. 9, 2000.
U.S. Appl. No. 10/246,087, filed Sep. 17, 2002.
U.S. Appl. No. 12/336,970, filed Dec. 17, 2008.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.

(56) References Cited

OTHER PUBLICATIONS

U.S. Appl. No. 12/607,191, filed Oct. 28, 2009.
U.S. Appl. No. 12/619,100, filed Nov. 16, 2009.
U.S. Appl. No. 12/665,081, filed Dec. 17, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/762,482, filed Apr. 19, 2010.
U.S. Appl. No. 12/766,476, filed Apr. 23, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/820,024, filed Jun. 23, 2010.
U.S. Appl. No. 12/821,253, filed Jun. 23, 2010.
U.S. Appl. No. 12/832,772, filed Jul. 8, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.

(56) References Cited

OTHER PUBLICATIONS

Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

\* cited by examiner

OPTICAL HYDROLOGY ARRAYS AND SYSTEM AND METHOD FOR MONITORING WATER DISPLACEMENT DURING TREATMENT OF PATIENT TISSUE

BACKGROUND

1. Technical Field

This application relates to optical spectrometry systems and, more particularly, to optical spectrometry systems applied to patient tissue to measure tissue hydration levels and to detect a signal indicative of water content.

2. Description of Related Art

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters (mm) to twelve millimeters (mm). Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

Thus, medical devices that apply electro-thermal energy for vessel sealing, ablation, coagulation are known in the art. Tissue conductance and permittivity are significant factors in the therapeutic effect of such medical devices that apply the electro-thermal energy to patient tissue. Displacement of water is correlated with changes in tissue conductance and permittivity and lack of control over such changes in tissue conductance and permittivity can lead to overdessication during vessel sealing procedures.

SUMMARY

To advance the state of the art with respect to application of electro-thermal energy to patient tissue, the present disclosure relates to a system and a method for monitoring water displacement during treatment of patient tissue.

In one embodiment, the system for monitoring water displacement in tissue during patient therapy includes a generator configured to supply electrosurgical energy to tissue, a spectrometer operably coupled to the generator, and a processor in operative communication with the generator and with the spectrometer. The spectrometer includes a light source for exposing tissue to light and a light sensor. The light sensor is configured to sense changes in light through tissue in response to tissue treatment and communicate such changes to the processor to determine tissue hydration levels. A plurality of optical fibers may be operably coupled to the generator and configured to communicate light between the generator and tissue. The plurality of optical fibers may be configured in an array. The spectrometer may be a near infrared spectrometer providing light in the near infrared wavelength range as the light source.

In one embodiment, the system may also include an optical temperature monitor. The optical temperature monitor may be in operative communication with the processor, and include at least one optical fiber operatively coupled to the optical temperature monitor. The one or more optical fibers are configured to enable the optical temperature monitor to monitor the temperature of the tissue where water displacement is optically monitored. The one or more optical fibers may be configured within a plurality of optical fibers wherein at least one optical fiber is operatively coupled to the light source to enable transmitting light towards the tissue and at least one optical fiber is configured to receive light reflected from the tissue and to transport the light to the light sensor. The plurality of optical fibers may be configured in an optical array. The plurality of optical fibers of the optical array may be configured to have an optic fiber distance between adjacent optical fibers. The optical fiber distance is within the range of about 0.25 millimeters (mm) to about 4.0 mm to optimize the transmission of light through tissue to determine hydration levels.

In one embodiment, the processor is configured to record and/or analyze changes in hydration of the tissue sensed by the spectrometer across the optic fiber distance. In addition, the processor may be configured to record and/or analyze changes in temperature of the tissue sensed by the optical temperature monitor. The sensed temperature may be used to calculate compensation for the temperature effect on hydration measured by the spectrometer.

In one embodiment, the system is incorporated in an electrosurgical pencil that includes a housing having proximal and distal ends, and a blade receptacle defined at a distal end of the housing for supporting an electrosurgical blade therein. The electrosurgical blade is disposed in optical communication with the light source and light sensor for monitoring hydration levels in tissue during operation of the electrosurgical pencil.

In one embodiment, the system is incorporated in an electrosurgical forceps that includes a pair of first and second jaw members disposed in pivotal relationship with respect to one another and attached to a distal end of at least one shaft. Each jaw member supports an electrically conductive surface thereon, at least one of the jaw members is disposed in optical communication with the light source and the other of the jaw members is disposed in optical communication with the light sensor for monitoring hydration levels in tissue during operation of the electrosurgical forceps.

The present disclosure relates also to a method for monitoring water displacement in tissue during patient therapy. The method includes the steps of providing a spectrometer including a light source in operative communication with patient tissue, generating light from the light source, reflecting the light through the patient tissue; and receiving the light reflected through the patient tissue with a light sensor. The method may include supplying electrosurgical energy to patient or subject tissue utilizing an energy source, sensing changes in light through the tissue in response to tissue treatment, and determining changes in tissue hydration levels based on the sensed changes in light through the tissue. In addition, the method may include providing a processor for analyzing the sensed changes in light through the tissue, and determining the changes in hydration levels in the tissue based on the sensed changes in light through the tissue. The processor may operatively communicate with the spectrometer to regulate the supply of electrosurgical energy to the tissue. The method may also include configuring a plurality of optical fibers in an array, wherein the array enables at least one of the plurality of optical fibers operatively coupled to the light source and enables at least one optical fiber of the plurality of optical fibers to be configured to enable transporting light reflected from the tissue to be separated to effect an optic fiber distance within the tissue. That is, the processor may be operatively coupled to the spectrometer and/or the supply of electrosurgical energy.

In one embodiment, the method includes providing an optical temperature monitor, providing at least one optical fiber operatively coupled to the optical temperature monitor, and monitoring the temperature of the tissue where water displacement is optically monitored. Knowledge of the temperature of the tissue can be used to provide more accurate measurement of tissue hydration.

In one embodiment, the present disclosure relates to an electrically conductive member for use with an electrosurgical instrument. The electrically conductive member includes a surface configured to engage patient tissue and adapted to connect to a source of electrosurgical energy. The electrically conductive member also includes at least one optical transmitter that is configured to propagate light through patient tissue and at least one corresponding optical sensor configured to sense changes in reflected light propagating through patient tissue during operation of the electrosurgical instrument and relating the changes in reflected light through patient tissue to hydration levels in tissue.

BRIEF DESCRIPTION OF THE DRAWINGS

Various embodiments are described herein with reference to the drawings:

FIG. 12B' is an end view of the electrically conductive member of FIG. 12A for a bipolar electrosurgical forceps;

FIG. 12C' is a view of the electrically conductive member of FIG. 12B' taken along section line 12C'-12C';

DETAILED DESCRIPTION

The present disclosure relates to a system and method for detecting water displacement and/or water hydration levels in tissue by arranging optic fibers in an array on the tissue contacting surfaces. Optic fibers are configured at one end to connect the fibers to a light source and at an opposite end to terminate in an array such that the light is transmitted into the tissue may be measured and/or monitored. Several light sensing optic fibers may also be included in the array and disposed in close proximity to the lens of the fiber optic that is the source. The end of the sensing optic fiber opposite the array is connected to a spectrometer. The configuration of the array can be designed into many different configurations and is not necessarily limited in this disclosure. The configuration may be dependent on the type of tissue and the geometry of the application. Applications include by are not limited to medical devices that use electro-thermal energy. The spacing and placement of the optical fiber elements of the optical array are specified such that discrete changes in hydration of the tissue over time can be recorded. These recorded discrete hydration changes together with the known array geometry can be analyzed (for example, by computer) to provide information on the displacement of water in the tissue. The source and detected wavelengths are selected to optimize the detection of water.

One application of this type of optical array is the placement of the array in close proximity to a thermal ablation probe. The displacement of water is correlated with changes in tissue conductance and permittivity. Tissue conductance and permittivity are significant factors in the therapeutic effect of medical devices that use electro-thermal energy.

A series of probes measures the hydration of a multitude of tissues. A probe or probes are placed in an array at a location where the sensors receiving the reflected signal are placed in the array so that changes in hydration can be monitored. Dynamic changes of hydration during energy treatment of tissue can be recorded, analyzed, and utilized to control delivery of electrosurgical energy during the course of tissue treatment.

Figure 1:
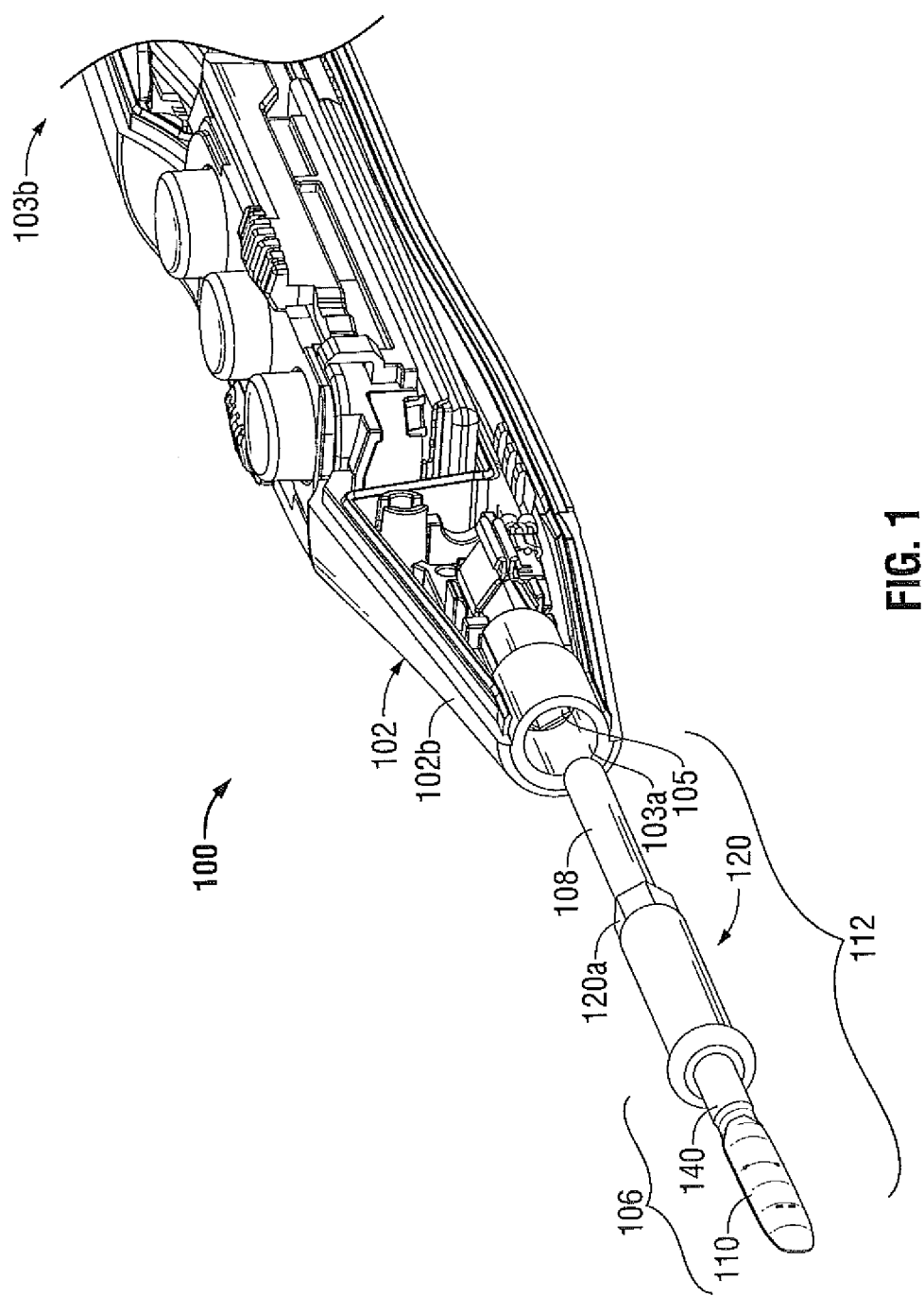
FIG. 1 is a perspective view of an electrode assembly of an electrosurgical pencil according to the present disclosure illustrating one embodiment of an end effector assembly having an optical transmitter positioned to propagate light through patient tissue and optical sensors positioned to sense at least a portion of the light propagating through patient tissue for monitoring hydration levels in tissue during operation of the electrosurgical pencil.

Turning now to FIG. 1, there is illustrated a partial view of electrosurgical pencil 100 that includes a housing 102 defining an open distal end 103a for selectively receiving proximal end 108 of electrocautery blade 106 therein. Open distal end 103a defines a blade receptacle 105 for blade 106. (The proximal end 103b of the housing 103 is not entirely shown).

In one embodiment, electrocautery blade 106 is supported in a collar 120. Collar 120 is positioned between distal end 110 and proximal end 108 of electrocautery blade 106. Collar 120 has a shaped outer surface 120a configured and dimensioned to complement the inner profile of receptacle 105 of open distal end 103a. In one embodiment, the open distal end 103a of housing 102 defines a hexagonally-shaped inner profile of receptacle 105 and collar 120 defines a hexagonal outer surface 120a. The blade 106 and the collar 120 define an electrocautery end effector assembly 112 that is operatively connectable to the blade receptacle 105.

Such an electrosurgical pencil is disclosed in commonly owned US Patent Application Publication No. 2006/0178667, U.S. patent application Ser. No. 11/337,990 by Sartor et al., entitled "ELECTROSURGICAL PENCIL WITH ADVANCED ES CONTROLS," the entire contents of which is incorporated by reference herein.

Blade receptacle 105 is defined at the distal end 103a of the housing for supporting the electrosurgical blade 106 therein.

The electrosurgical blade 106 is configured to be connected to a source of electrosurgical energy, e.g., an electrosurgical generator, not shown.

Turning initially to FIGS. 3A through 4B, there are various illustrated embodiments of optical transmitters and optical sensors for use with end effector assembly 112. As defined herein, an optical transmitter includes, but is not limited to, small diameter optical fibers, e.g., having a diameter ranging up to about 1 millimeter (mm); large diameter optical fibers, e.g. having a diameter ranging up to about 2 mm; prisms that reflect at least a portion of light propagating therethrough, optical fibers having at least one end with a tapered configuration to function as a prism, light-emitting electronic devices such as a light-emitting diodes (LED), or electrical cables that transmit electrical signals that provide optical information from a light source. As defined herein, an electrical cable is capable of providing optical communication between a light source and a light-emitting electronic device. Photo-electric detectors convert photonic signals to electrical signals, and light-emitting electronic devices such as light-emitting diodes convert electrical signals to photonic signals.

Such optical transmitters may be configured as single members or in an assembly of one or more members of the same category in optical communication with one another or in an assembly of one or more members of different categories in optical communication with one another.

As defined herein, an optical sensor includes, but is not limited to, small diameter optical fibers, e.g., having a diameter ranging up to about one (1) millimeter (mm); large diameter optical fibers, e.g. having a diameter ranging up to about two (2) mm; prisms that reflect at least a portion of light propagating therethrough, optical fibers having at least one end with a tapered configuration that functions as a prism, light-sensing electronic devices such a photo-electric detector or photosensor, or electrical cables that transmit electrical signals that provide optical information from a photo-electric detector. Such photoelectric detectors may be made from, for example, gallium arsenide (GaAs), indium phosphide (InP), gallium phosphide (GaP), indium gallium arsenide (InGaAs), silicon germanium (SiGe), germanium (Ge), germanium tin (GeSn), sulfur germanium tin (SGeSn) and the like. As defined herein, an electrical cable is capable of providing optical communication between a photo-electric detector and a light-emitting electronic device. Photo-electric detectors convert photonic signal to electrical signals, and light-emitting electronic devices such as light-emitting diodes convert the electrical signals to photonic signals.

Similarly, such optical sensors may be configured as single members or in an assembly of one or more members of the same category in optical communication with one another or in an assembly of one or more members of different categories in optical communication with one another.

Optical sensors include, but are not limited to, optical detectors that are mostly quantum devices in which an individual photon produces a discrete effect; photoresistors or light dependent resistors in which resistance is a function of light intensity; photodiodes operating in a photovoltaic mode or in a photoconductive mode; photovoltaic cells or solar cells producing a voltage and an electric current when illuminated; photomultiplier tubes containing a photocathode that emits electrons when illuminated and wherein the electrons may be amplified by a chain of dynodes; phototubes containing a photocathode that emits electrons when illuminated wherein the tube conducts a current proportional to the light intensity; light-emitting devices (LEDs) that are reverse-biased to act as photodiodes; phototransistors that function as amplifying photodiodes; optical detectors that function as thermometers converting heat of incoming radiation to an electrical current, such as pyroelectric detectors, Golay cells, thermocouples and thermistors Additionally, as defined herein, an optical transmitter may also function alternately as an optical sensor to serve as a dual function optical transmitter and optical receiver. A dual function optical transmitter and optical receiver may include a multiplexer device.

Returning specifically to FIG. 3A, optical transmitter 202 includes one or more optical fibers e.g., optical fibers 204a, 204b, and 204c and/or one or more light reflecting prisms 206 in optical communication with corresponding optical fibers 204a, 204b and/or 204c. The optical transmitter 202 may include a large diameter single optical fiber 208 in optical communication with patient tissue (not shown). The diameter of optical fiber 208 ranges up to about 3 mm. Light 10 is illustrated propagating through the optical fibers 204a, 204b and 204c to prism 206 wherein the light 10 is reflected by the prism 306 to a large diameter single optical fiber 208 propagates the light to patient tissue.

Figure 3A:
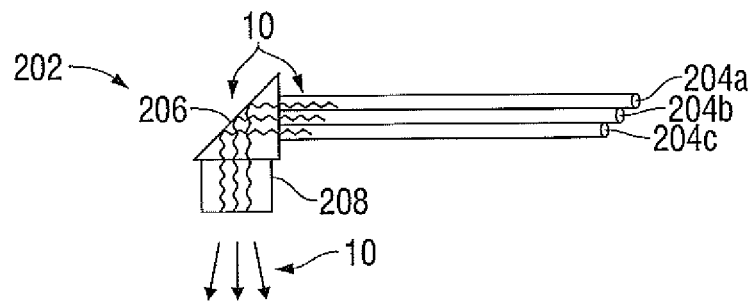
FIG. 3A is a schematic view of one embodiment of an optical transmitter wherein light is reflected by a prism.
Figure 3B:
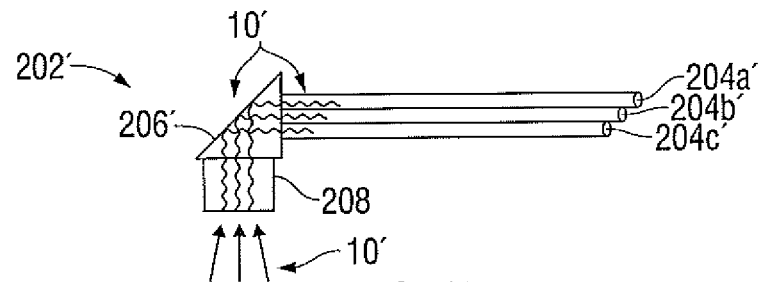
FIG. 3B is a schematic view of one embodiment of an optical sensor wherein light is reflected by a prism.

FIG. 3B illustrates an optical sensor 202' that also includes one or more optical fibers e.g., optical fibers 204a, 204b, and 204c and/or one or more light reflecting prisms 206 in optical communication with corresponding optical fibers 204a', 204b' and/or 204c'. The optical sensor 202 may include a large diameter single optical fiber 208 in optical communication with patient tissue (not shown). Optical sensor 202' differs from optical transmitter 202 in that light 10' travels in the reverse direction as compared to light 10. More particularly, light 10' is illustrated propagating from the patient tissue (again not shown) through the large diameter optical fiber 208 to prism 206 wherein the light 10' is reflected by the prism 206 to optical fibers 204a', 204b' and 204c'. Additionally, optical fibers 204a', 204b' and 204c' may have diameters which differ from one another so as to propagate differing wavelengths of light. The diameters of optical fibers 204a', 204b' and 204c' may also differ from the diameters of optical fibers 204a, 204b and 204c of optical transmitter 202 described with respect to FIG. 3A.

Figure 3C:
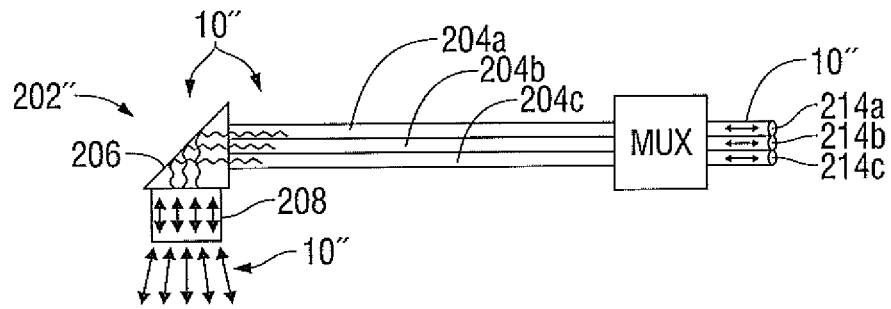
FIG. 3C is a schematic view of one embodiment of a dual-function optical transmitter and optical sensor wherein light is reflected by a prism.

FIG. 3C illustrates one embodiment of a dual function optical transmitter and optical sensor 202" wherein light 10" may propagate to patient tissue (again not shown) and alternately propagate from patient tissue. More particularly, dual-function optical transmitter and optical sensor 202" is substantially identical to optical transmitter 202 and optical sensor 202' except for the inclusion of optical multiplexer 210 in the path of optical fibers 204a, 204b and 204c. The optical multiplexer (MUX) 210 is in optical communication with proximal optical fibers 214a, 214b and 214c and with distal optical fibers 204a, 204b and 204c In the transmission phase of operation, light 10" propagates from the proximal side of MUX 210 through the proximal optical fibers 214a, 214b and 214c through the MUX 210 to the distal optical fibers 204a, 204b and 204c. As is the case for optical transmitter 202, light 10" is reflected by the prism 206 to propagate through the large optical fiber 208 to pass through patient tissue.

In the sensing phase of operation, light 10" propagates from patient tissue where the light 10" is detected by the large diameter optical fiber 208 and propagates to the prism 206 wherein the light 10" is reflected by the prism 206 to distal optical fibers 204a, 204b and 204c. The light 10" propagates to the MUX 210 where the light is selectively propagated by switching to at least one or more of the proximal optical fibers 214a, 214b and 214c.

Figure 4A:
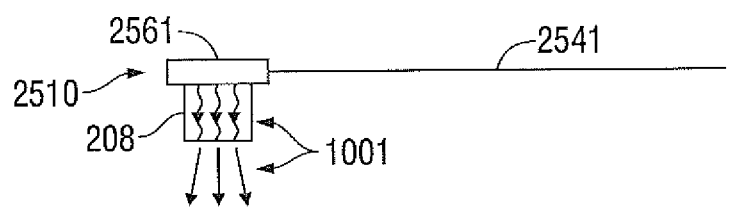
FIG. 4A is a schematic view of one embodiment of an optical transmitter wherein light is transmitted by a light emitting diode.

FIG. 4A illustrates an alternate embodiment of an optical transmitter 2510. More particularly, optical transmitter 2510 includes electrical cable 2541 that is capable of providing optical communication between a light source (to be described below with respect to FIGS. 18-20), and a light-emitting electronic device 2561 such as a light-emitting diode. A photo-electric detector (not shown) converts a photonic signal to an electrical signal. The light-emitting electronic device 256 converts the electrical signal to a photonic signal resulting in light 101 being emitted from the light-emitting electronic device 256 to propagate through large diameter optical fiber 208 to patient tissue (also not shown).

Figure 4B:
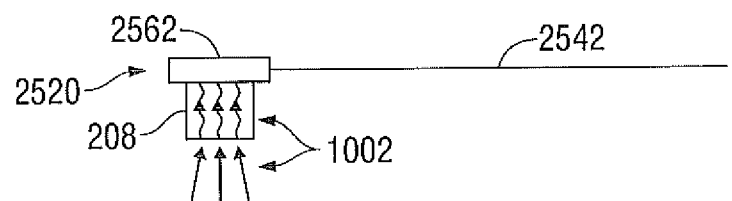
FIG. 4B is a schematic view of one embodiment of an optical sensor wherein light is sensed by a light emitting diode.

FIG. 4B illustrates an alternate embodiment of an optical sensor 2520. More particularly, optical sensor 2520 includes electrical cable 2542 that is capable of providing optical communication between photo-electric detector 2562 and a light detector (to be described below with respect to FIGS. 18-20). Light 102 propagating through patient tissue (not shown) propagates to large diameter optical fiber 208 in contact with patient tissue. The photo-electric detector 2520 detects the light 102 propagating through the large diameter optical fiber 208 and converts the photonic signal to an electrical signal. The electrical signal communicates with the light detector (to be described below).

Figure 2A:
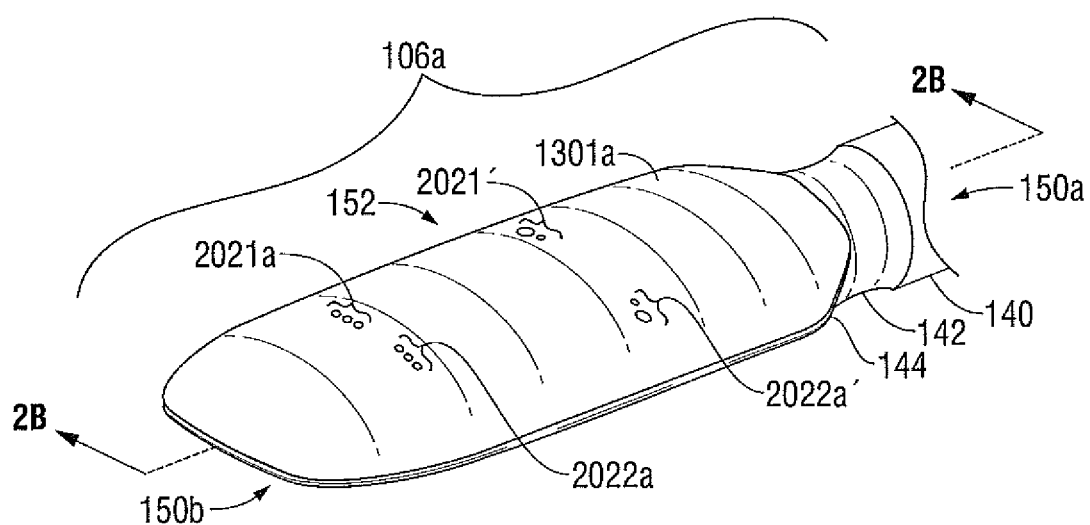
FIG. 2A is a perspective view an ES pencil blade of the end effector assembly of FIG. 1.
Figure 2B:
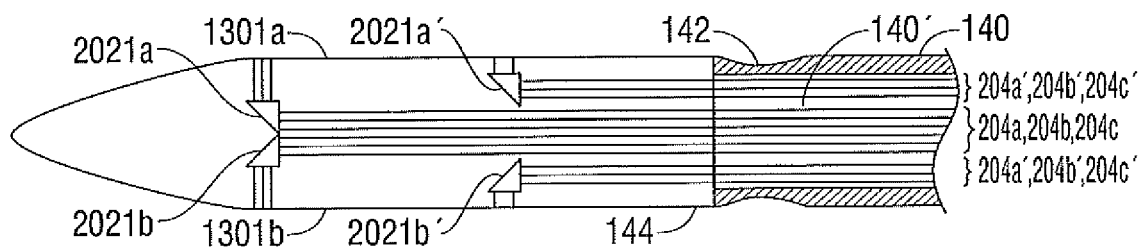
FIG. 2B is a cross-sectional view of the pencil blade of the end effector assembly taken along section line 2B-2B of FIG. 2A.

Returning to FIGS. 2A and 2B, one embodiment of electrocautery blade 106 is shown. More particularly, electrocautery blade 106a defines a proximal end 150a and a distal end 150b. The blade 106a has a substantially planar configuration having a generally convex lateral cross-section defining one or more peripheral edges 120 and one or more lateral surfaces, e.g., first surface 1301a and second surface 1301b. The blade 106a includes a cylindrical shaft 140 defining a hollow central region 140' therewithin and extending to a proximal end 144 of substantially planar region 152 of the blade 106a. The hollow shaft 140 extends to the substantially planar region 152 to define a circumferential recess 142 around the outer surface of the hollow shaft 140.

The electrosurgical blade 106a is configured with one or more optical transmitters 202 positioned to propagate light 10 through patient tissue and one or more optical sensors 202' positioned to sense at least a portion of the light 10' propagating through patient tissue for monitoring hydration levels in tissue during operation of the electrosurgical pencil 100.

More particularly, the electrosurgical blade 106a is configured wherein optical transmitters 2021a and 2022a (shown partially) propagate light through patient tissue via the first lateral surface 1301a while optical transmitters 2021b (2022b, not shown) propagate light through patient tissue via the second lateral surface 1301b, Optical transmitters 2021a, 2022a, 2021b (and 2022b, not shown) are configured with prism 206 and the optical fibers described with respect to optical transmitter 202 in FIG. 3A.

Similarly, the electrosurgical blade 106a is configured wherein optical sensors 2021a' and 2022a' (shown partially) sense at least a portion of the light propagating through the patient tissue via the first lateral surface. 1301a while optical sensors 2021b' (and corresponding optical sensors not shown) sense at least a portion of the light propagating through the patient tissue via the second lateral surface 1301b. Optical sensors 2021a', 2022a', 2021b' (and corresponding optical sensors not shown) are also configured with prism 206 and the optical fibers described with respect to the optical sensor 202' in FIG. 3B. As indicated, the diameters of the sensing optical fibers 204a', 204b', 204c' may differ from one another. The optical sensors 2021a' and 2021b' may be positioned proximally on the electrosurgical blade 106a with respect to the optical transmitters 2021a and 2021b.

The transmission optical fibers 204a, 204b, 204c and the sensing optical fibers 204a', 204b', 204c' are routed through the hollow central region 140' of the shaft 140 and further through the housing 102.

Figure 2C:
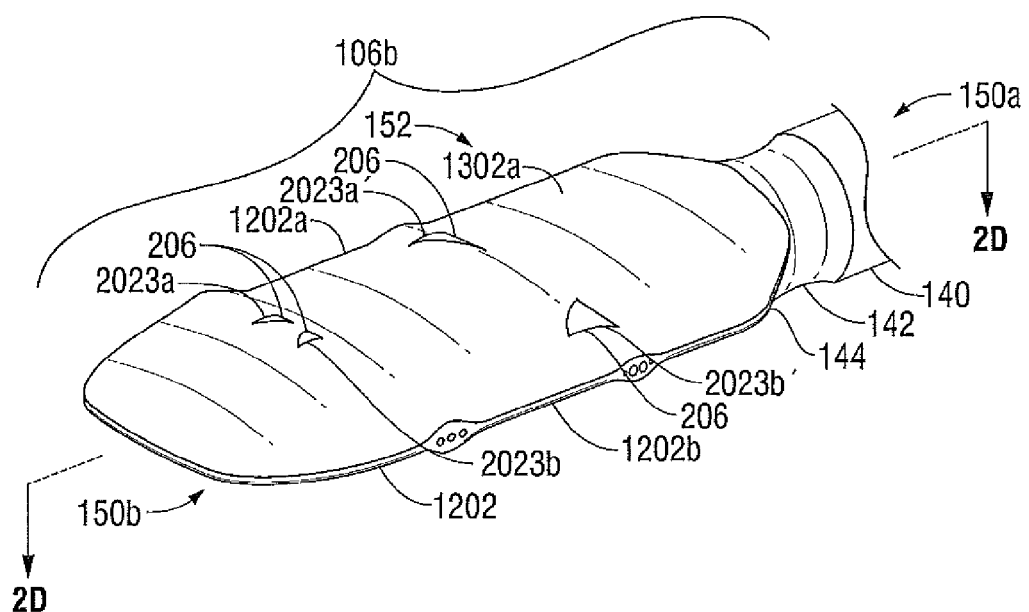
FIG. 2C is a perspective view of another embodiment of the pencil blade of the electrocautery end effector assembly of FIG. 1 having an optical transmitter and an optical sensor.
Figure 2D:
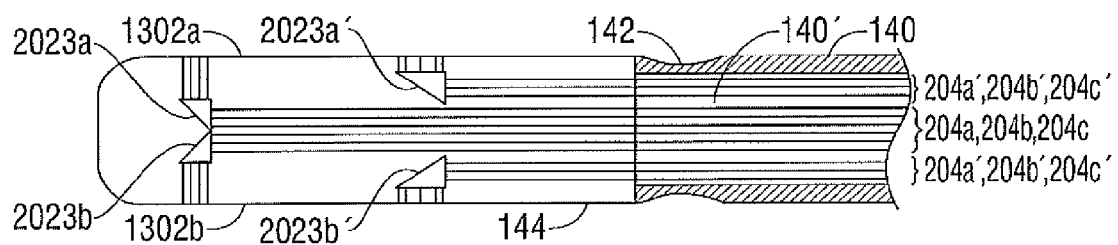
FIG. 2D is a cross-sectional view of the pencil blade of the electrocautery end effector assembly taken along section line 2D-2D of FIG. 2C

Turning now to FIGS. 2C and 2D, there is illustrated another embodiment of electrocautery blade 106. More particularly, electrocautery blade 106b again defines proximal end 150a and distal end 150b. The blade 106b has a substantially planar configuration having a generally convex lateral cross-section defining at least one peripheral edge 1202 and at least one lateral surface, e.g., first surface 1302a and second surface 1302b (not explicitly shown on the opposing side of first surface 1302a). The blade 106b includes cylindrical shaft 140 defining hollow central region 140' therewithin and extending to proximal end 144 of substantially planar region 152 of the blade 106b. The hollow shaft 140 extends to the substantially planar region 152 to define a circumferential recess 142 around the outer surface of the hollow shaft 140.

The electrosurgical blade 106b is again configured with at least one optical transmitter 202 positioned to propagate light 10 through patient tissue and at least one optical sensor 202' positioned to sense at least a portion of the light 10' propagating through the patient tissue for monitoring hydration levels in tissue during operation of the electrosurgical pencil 100.

More particularly, the electrosurgical blade 106b is configured wherein optical transmitters 2023a and 2023b propagate light through the patient tissue via first and second lateral portions 1202a and 1202b, respectively, of peripheral edge 1202. Additionally, the electrosurgical blade 106b is configured wherein optical sensors 2023a' and 2023b' sense at least a portion of the light propagating through the patient tissue via first and second lateral portions 1202a and 1202b, respectively, of peripheral edge 1202.

Optical transmitters 2023a and 2023b are configured with prism 206 and the optical fibers described with respect to optical transmitter 202 in FIG. 3A. Optical sensors 2023a' and 2023b' are also configured with prism 206 and the optical fibers described with respect to the optical sensor 202' in FIG. 3B, except that large diameter single optical fiber 208 is replaced by more than one smaller diameter optical fibers similar to 204a', 204b', 204c'. As indicated, the diameters of the sensing optical fibers 204a', 204b', 204c' may differ from one another. The optical sensors 2023a' and 2023b' may be positioned on the electrosurgical blade 106b proximally with respect to optical transmitters 2023a and 2023b.

The transmission optical fibers 204a, 204b, 204c and the sensing optical fibers 204a', 204b', 204c' are routed through the hollow central region 140' of the shaft 140 and further through the housing 102.

Figure 5A:
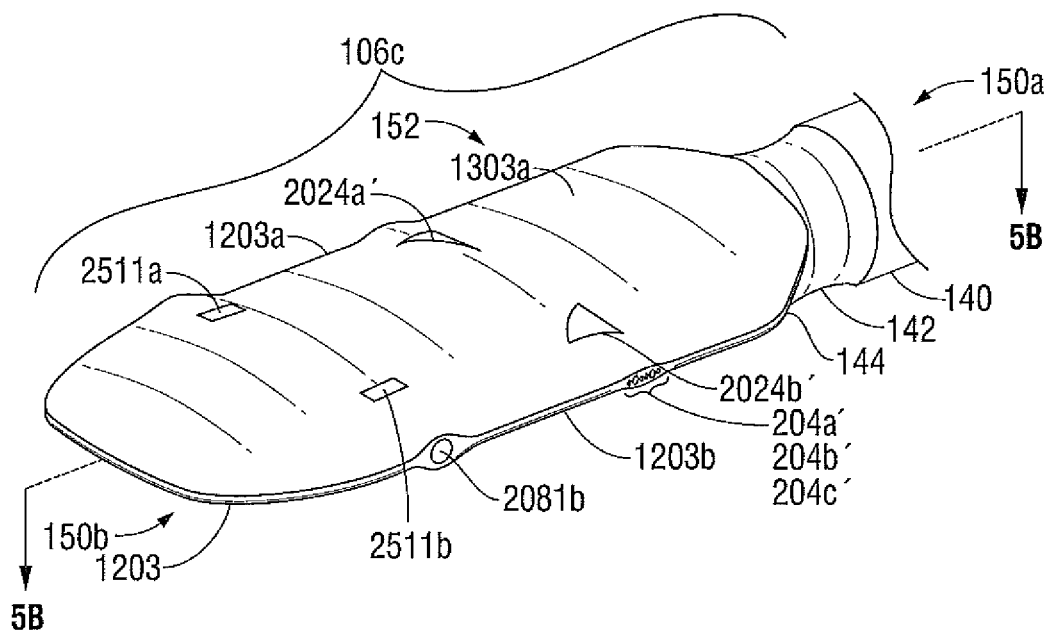
FIG. 5A is a perspective view of another embodiment of the pencil blade of the end effector assembly of FIG. 1 having an optical transmitter and an optical sensor.
Figure 5B:
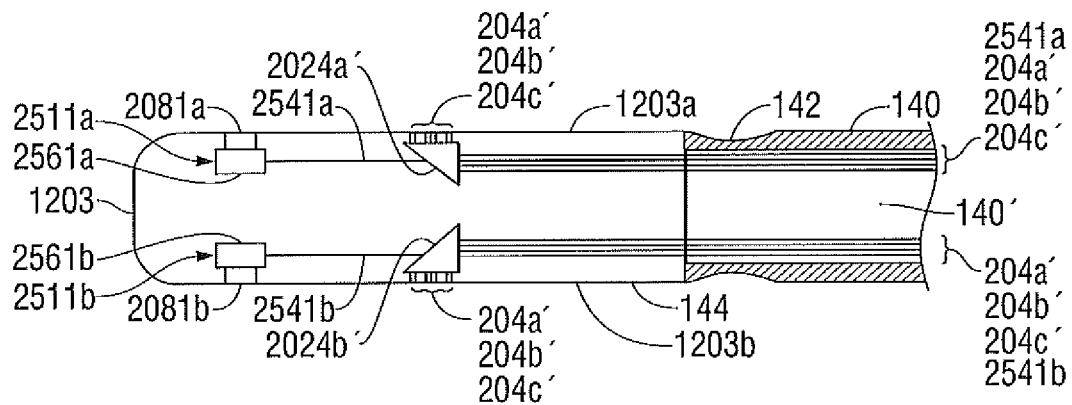
FIG. 5B is a cross-sectional view of the pencil blade of the end effector assembly taken along section line 5B-5B of FIG. 5A.

Turning now to FIGS. 5A and 5B, there is illustrated still another embodiment of electrocautery blade 106. More particularly, electrocautery blade 106c again defines proximal end 150a and distal end 150b. The blade 106c again has a substantially planar configuration having a generally convex lateral cross-section defining at least one peripheral edge 1203 and at least one lateral surface, e.g., first surface 1303a and a second surface not explicitly shown on the opposing side of first surface 1303a. The blade 106c again includes cylindrical shaft 140 defining hollow central region 140' therewithin and extending to proximal end 144 of substantially planar region 152 of the blade 106c. The hollow shaft 140 extends to the substantially planar region 152 to define a circumferential recess 142 around the outer surface of the hollow shaft 140.

In contrast to electrosurgical blades 106a and 106b, the electrosurgical blade 106c is configured with at least one optical transmitter 2510 positioned to propagate light 1001 through patient tissue, but, in a similar manner as with respect to electrosurgical blades 106a and 106b, with at least one optical sensor 202' positioned to sense at least a portion of the light 10' propagating through the patient tissue for monitoring hydration levels in tissue during operation of the electrosurgical pencil 100.

More particularly, the electrosurgical blade 106c is configured wherein optical transmitters 2511a and 2511b propagate light through the patient tissue via first and second lateral portions 1203a and 1203b, respectively, of peripheral edge 1203. Thus, the optical transmitters 2511a and 2511b include electrical cables 2541a and 2541b and light-emitting electronic devices 2561a and 2561b and large diameter optical fibers 2081a and 2081b, respectively, as described with respect to optical transmitter 2510 in FIG. 4A. Additionally, the electrosurgical blade 106c is configured wherein optical sensors 2024a' and 2024b' sense at least a portion of the light propagating through the patient tissue via first and second lateral portions 1203a and 1203b, respectively, of peripheral edge 1203.

Optical sensors 2024a' and 2024b' are also configured with prism 206 and the optical fibers described with respect to the optical sensor 202' in FIG. 3B, except that large diameter single optical fiber 208 is replaced by more than one smaller diameter optical fibers similar to 204a', 204b', 204c'. As indicated, the diameters of the sensing optical fibers 204a', 204b', 204c' may differ from one another.

The transmitting electrical cables 2541a and 2541b and the sensing optical fibers 204a', 204b', 204c' are again routed through the hollow central region 140' of the shaft 140 and further through the housing 102.

Figure 6A:
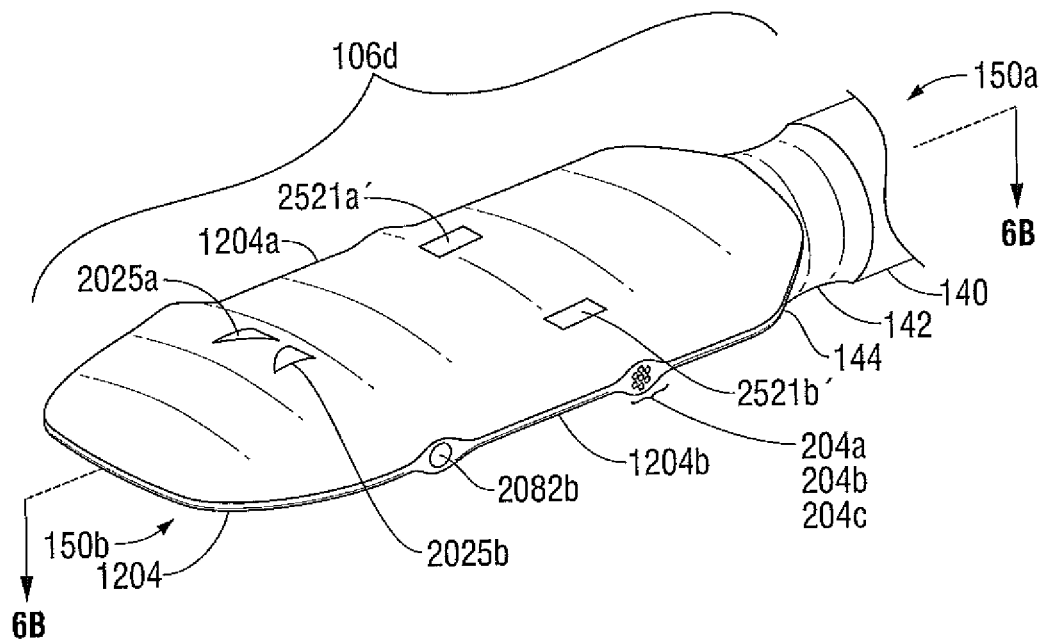
FIG. 6A is a perspective view of another embodiment of the pencil blade of the end effector assembly of FIG. 1 having an optical transmitter and an optical sensor.
Figure 6B:
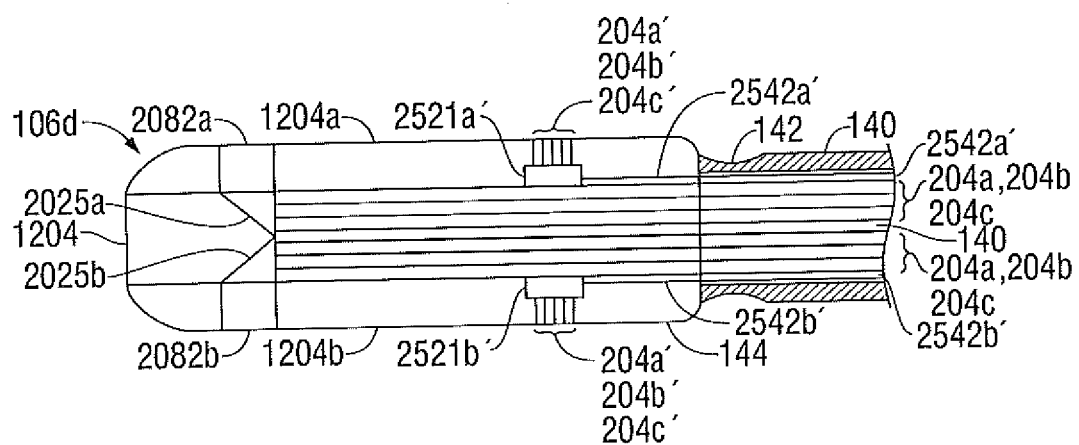
FIG. 6B is a cross-sectional view of the pencil blade of the electrocautery end effector assembly taken along section line 6B-6B of FIG. 6A.

FIGS. 6A and 6B illustrate yet another embodiment of electrocautery blade 106. More particularly, electrocautery blade 106d again defines proximal end 150a and distal end 150b. The blade 106d has a substantially planar configuration having a generally convex lateral cross-section defining at least one peripheral edge 1204 and at least one lateral surface, e.g., first surface 1304a and a second surface not explicitly shown on the opposing side of first surface 1304a. The blade 106d includes cylindrical shaft 140 defining hollow central region 140' therewithin and extending to proximal end 144 of substantially planar region 152 of the blade 106c. The hollow shaft 140 extends to the substantially planar region 152 to define a circumferential recess 142 around the outer surface of the hollow shaft 140.

In contrast to electrosurgical blades 106a, 106b or 106c, the electrosurgical blade 106d is configured with at least one optical transmitter 202 positioned to propagate light 10 through patient tissue, but, with at least one optical sensor 2520 positioned to sense at least a portion of the light 1002 propagating through the patient tissue for monitoring hydration levels in tissue during operation of the electrosurgical pencil 100.

More particularly, the electrosurgical blade 106d is configured wherein optical transmitters 2025a and 2025b propagate light through the patient tissue via first and second lateral portions 1204a and 1204b, respectively, of peripheral edge 1204. Thus, the optical transmitters 2025a and 2025b include large diameter optical fibers 2082a and 2082b, respectively, as described with respect to optical transmitter 202 in FIG. 3A.

Optical sensors 2025a and 2025b are also configured with prism 206 and the optical fibers described with respect to the optical sensor 202' in FIG. 3A.

Additionally, the electrosurgical blade 106d is configured wherein optical sensors 2521a' and 2521b' sense at least a portion of the light propagating through the patient tissue also via first and second lateral portions 1204a and 1204b, respectively, of peripheral edge 1204. The optical sensors 2521a' and 2521b' include the electrical cables 2542a' and 2542b' and photo-electric detectors 2562a' and 2562b' and each with a plurality of optical fibers similar to optical fibers 204a', 204b' and 204c' on the first and second portions 1204a and 1204b, respectively, of the lateral edge 1204. as described with respect to optical sensor 2520 in FIG. 4B, thereby sensing at least a portion of the light propagating through the patient tissue.

Additionally, the electrosurgical blade 106d is configured wherein optical sensors 2521a' and 2521b' may be positioned proximally on the electrosurgical blade 106d with respect to the optical transmitters 2025a and 2025b.

The transmitting optical fibers 204a, 204b, 204c and the sensing electrical cables 2542a and 2542b are routed through the hollow central region 140' of the shaft 140 and further through the housing 102.

FIGS. 7-11 and 12A, 12B, 12C and 13 illustrate various embodiments of an electrically conductive member 300 for use with an electrosurgical instrument. The electrically conductive member 300 has a surface 302 that is configured to be in contact with patient tissue (not shown) and to be connected to a source of electrosurgical energy (not shown), As described in more detail below, the electrically conductive member 300 is configured with one or more optical transmitters positioned in an array to propagate light through patient tissue and one or more optical sensors positioned in an array to sense via reflectance by the patient tissue at least a portion of the light propagating through the patient tissue for monitoring hydration levels in tissue during operation of the electrosurgical pencil.

Figure 7:
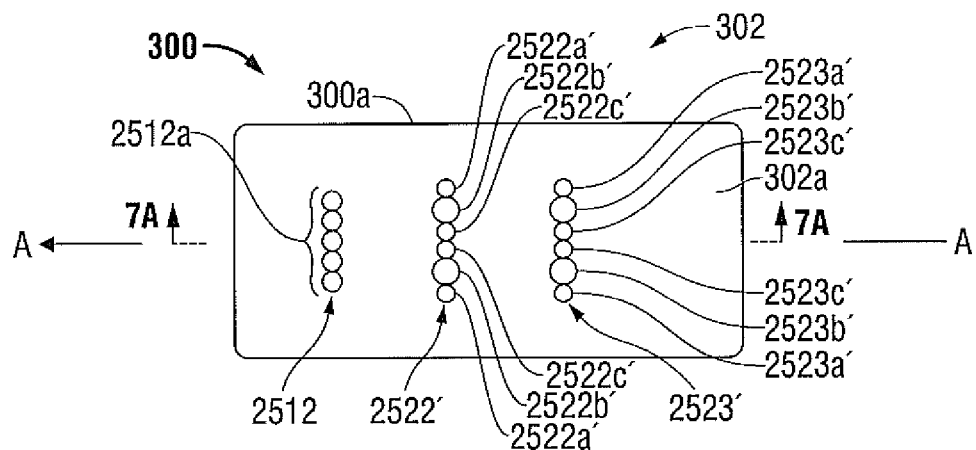
FIG. 7 is a schematic view of one embodiment of an electrically conductive member for use with an electrosurgical instrument according to the present disclosure in which one optical transmitter and two optical sources are disposed substantially linearly on a surface of the electrically conductive member.
Figure 7A:
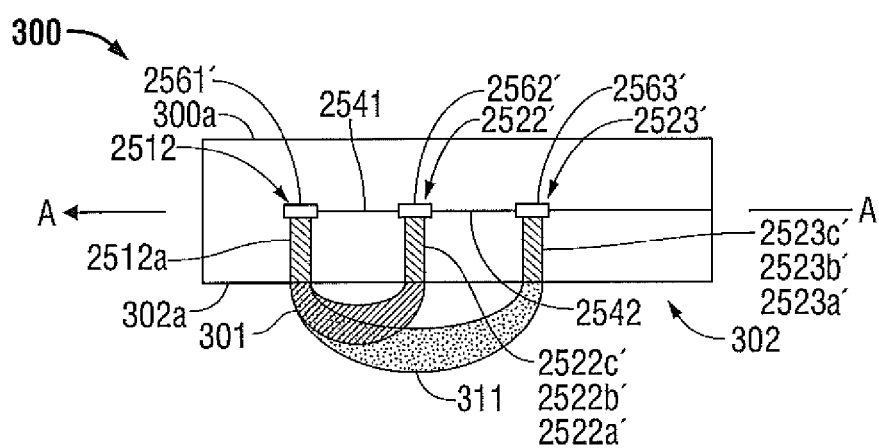
FIG. 7A is a schematic view of the electrically conductive member of FIG. 7 taken along section line 7A-7A.

Turning particularly to FIGS. 7 and 7A, and in conjunction with FIGS. 4A and 4B, electrically conductive member 300a has surface 302a that is configured to be in contact with, or to engage with, patient tissue (not shown) and adapted to connect to a source of electrosurgical energy (not shown), The surface 302a is configured with one or more optical transmitters 2512 positioned in an array to propagate light through patient tissue and at least one optical sensor, e.g., two optical sensors 2522 and 2523 positioned in an array, configured to sense changes in reflected light, e.g., via reflectance by the patient tissue, at least a portion of the light propagating through the patient tissue during operation of the electrosurgical instrument and relating the changes changes in reflected light to hydration levels in tissue during operation of the electrosurgical pencil.

The optical sensors 2522' and 2523' may include first optical fibers 2522a' and 2523a', second optical fibers 2522b' and 2523b', and third optical fibers 2522c' and 2523c', respectively, wherein the diameter of the first optical fibers 2522a' and 2523a' differs from the diameter of the second optical fibers 2522b' and 2523b', and the diameter of the third optical fibers 2522c' and 2523c' differs from the diameters of the first and second optical fibers.

The optical transmitters 2512 are disposed substantially linearly to form on the surface a single line of optical fibers 2512a that is disposed distally from the two optical sensors 2522' and 2523. The optical fibers of optical sensors 2522' and 2523' are disposed substantially linearly to form first and second lines of optical fibers 2522a', 2522b', 2522c' and 2523a', 2523b', 2523c', respectively. The optical transmitters 2512 may be disposed substantially linearly relative to one another along an axis "A" defined through the electrically conductive member 300a from a proximal end to a distal end thereof. The optical transmitters 2512 may be disposed distally relative to the optical sensors 2522' and 2523'. The optical sensors 2522' and 2523' may correspond to the optical transmitters 2512.

As illustrated in FIG. 7A, in a similar manner as with respect to the optical transmitter 2510 described with respect to FIG. 4A, the optical transmitter 2512 includes electrical cable 2541, light-emitting electronic device 2561 and the single line of optical fibers 2512a. In addition, in a similar manner as with respect to the optical sensor 2520 described with respect to FIG. 4B, optical sensors 2522' and 2523' include electrical cables 2542' and 2543', photo-electric detector 2562' and 2563', and the optical fibers 2522a', 2522b', 2522c' and 2523a', 2523b', 2523c', respectively.

Upon emission of light from the light-emitting electronic device 2561, light path 301 propagates from the single line of optical fibers 2512a to first line of optical fibers 2522a', 2522b', 2522c' of first optical sensor 2522'. Similarly, light path 311 propagates from the single line of optical fibers 2512a to second line of optical fibers 2523a', 2523b', 2523c' of second optical sensor 2523'.

As explained below in more detail with respect to FIGS. 19-20, the different diameters of the optical fibers of the optical sensors 2522' and 2523' enable monitoring of water motility within the patient tissue during the electrosurgical procedure.

Figure 8:
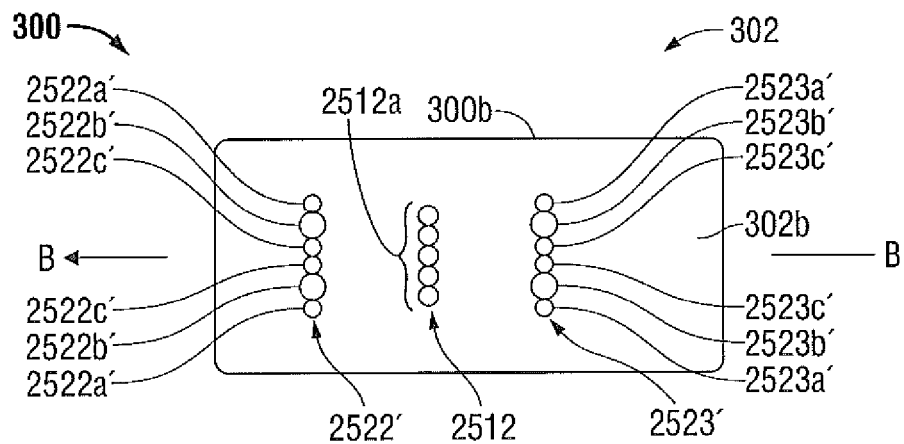
FIG. 8 is a schematic view of another embodiment of an electrically conductive member for use with an electrosurgical instrument according to the present disclosure in which one optical transmitter and two optical sources are disposed substantially linearly on a surface of the electrically conductive member.

FIG. 8 illustrates an alternate embodiment of the electrically conductive member 300 having surface 302. More particularly, electrically conductive member 300b is an alternate embodiment of the electrically conductive member 300a described above with respect to FIGS. 7 and 7A. Again, the electrically conductive member 300b includes the at least two optical sensors 2522' and 2523'. The optical fibers 2522a', 2522b', 2522c' and 2523a', 2523b' 2523c' of the optical sensors 2522' and 2523', respectively are disposed substantially linearly to form on surface 302b first and second lines. The first line 2522' is distal from the second line 2523'.

Electrically conductive member 300b differs from electrically conductive member 300a in that the optical fibers 2512a of the optical transmitter 2512 are disposed substantially linearly to form a single line disposed between the first and second lines of the two or more optical sensors 2522' and 2523'. That is, the plurality of optical sensors 2522' and 2523' may be disposed substantially linearly along an axis "B" defined through the electrically conductive member 300b. The optical sensors 2522' and 2523' may be disposed substantially linearly relative to one another to form first and second lines of optical sensors on the surface 302b. The second line of optical sensors 2522' may be distal from the first line of optical sensors 2523'.

As illustrated in FIG. 7A, the optical transmitter 2512 forms a first light path in patient tissue. The first light propagates by reflectance in the patient tissue to the first optical sensor 2522' while the optical transmitter 2512 also forms a second light path in patient tissue, wherein the second light path propagates by reflectance in the patient tissue to the second optical sensor 2523'. The diameters of the optical fibers 2522a', 2522b', 2522c' may differ from one another. Similarly, the diameters of the optical fibers 2523a', 2523b', 2523c' may differ from one another to allow propagation of light of differing wavelengths.

The optical transmitter 2512 may also include the light-emitting electronic device 2561 and electrical cable 2541 described previously with respect to FIG. 4A while the optical sensors 2522', 2523' include the photo-electric detector 2562 and electrical cable 2542 described previously with respect to FIG. 4B.

Figure 9:
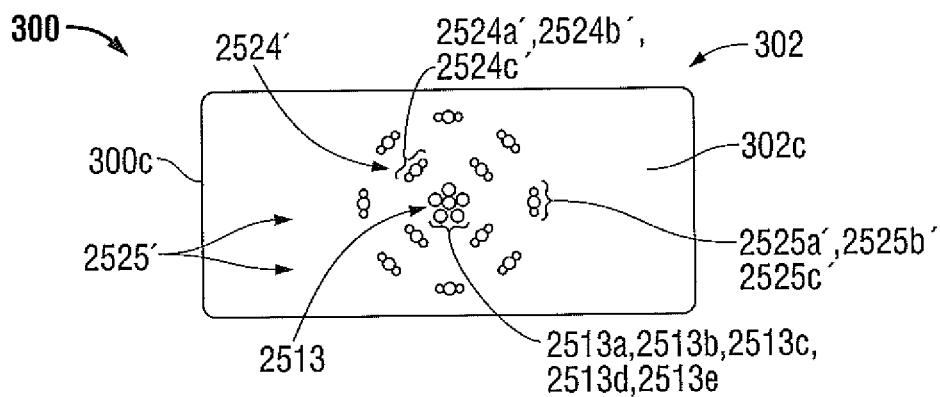
FIG. 9 is a schematic view of yet another embodiment of an electrically conductive member for use with an electrosurgical instrument according to the present disclosure having a circular array of optical sensors and an optical transmitter disposed on a surface of the electrically conductive member.

FIG. 9 illustrates yet another embodiment of the electrically conductive member 300 having surface 302. More particularly, electrically conductive member 300c includes one or more optical transmitters 2513 and two or more optical sensors, e.g., first optical sensor 2524' and second optical sensor 2525'. The optical transmitter 2513 and the first and second optical sensors 2524', 2525' are disposed in a pattern on surface 302c that includes at least a first plurality of optical fibers 2524a', 2524b', 2524c' of optical sensor 2524' in a circumferential arrangement and a second plurality of optical fibers 2525a', 2525b', 2525c' of optical sensor 2525' in a circumferentially substantially concentric arrangement with respect to the first plurality of optical fibers 2524a', 2524b', 2524c' of optical sensor 2524'. That is, the first plurality of optical sensors 2524' may be disposed in a first circumferential pattern on the surface 302c and the second plurality of optical sensors 2525' may be disposed in a second circumferential pattern on the surface 302c that is concentric to the first circumferential pattern of the first plurality of optical sensors 2524'.

Optical fibers 2513a, 2513b, 2513c, 2513c, 2513d, 2513e of optical transmitter 2513 are disposed substantially at the center of the substantially concentric arrangement of the first and second plurality of optical fibers 2524a', 2524b', 2524c' and 2525a', 2525b', 2525c' of the optical sensors 2524' and 2525', respectively. That is, the optical transmitter 2513 may be disposed substantially at the center of the concentric arrangement of the first and second circumferential patterns of the optical sensors 2524' and 2525', respectively.

In view of the light paths 301 and 311 illustrated in FIG. 7A, the optical transmitter 2513 forms multiple light paths in patient tissue distributed substantially radially away from the optical fibers 2513a, 2513b, 2513c, 2513c, 2513d, 2513e, The light propagates by reflectance in the patient tissue to the substantially concentric arrangement of the first and second plurality of optical fibers 2524a', 2524b', 2524c' and 2525a', 2525b', 2525c' of the optical sensors 2524' and 2525', respectively. The diameters of the plurality of optical fibers 2524a', 2524b', 2524c' and 2525a', 2525b', 2525c' may again differ from one another as explained above In addition, the optical transmitter 2513 may include the light-emitting electronic device 2561 and electrical cable 2541 described previously with respect to FIG. 4A while the optical sensors 2524', 2525' include the photo-electric detector 2562 and electrical cable 2542 described previously with respect to FIG. 4B.

Figure 10:
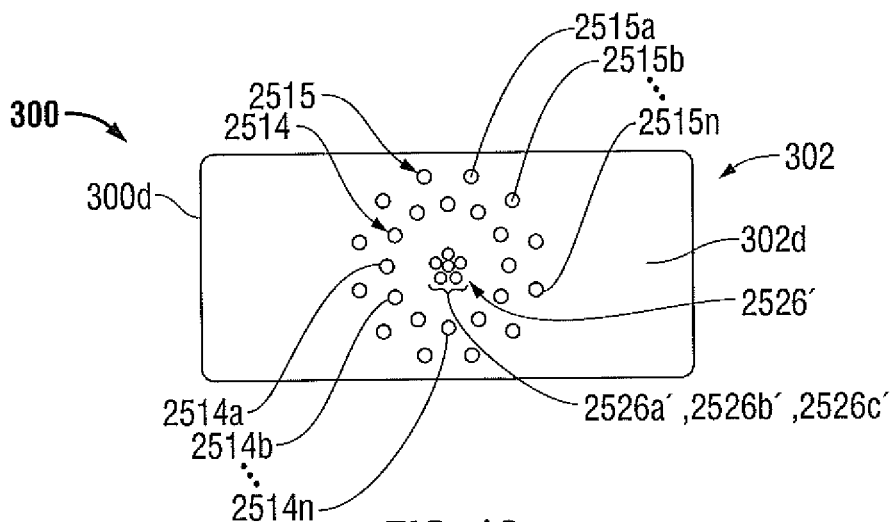
FIG. 10 is a schematic view of still another embodiment of an electrically conductive member for use with an electrosurgical instrument according to the present disclosure having a circular array of optical transmitters and an optical sensor disposed on a surface of the electrically conductive member.

FIG. 10 illustrates still another embodiment of the electrically conductive member 300 having surface 302. More particularly, electrically conductive member 300d includes two or more optical transmitters, e.g., first optical transmitter 2514 and second optical transmitter 2515. The optical transmitters 2514, 2515 are disposed in a pattern on surface 302d that includes at least a first plurality of optical fibers 2514a, 2514b . . . 2514n of optical transmitter 2514 in a circumferential arrangement and a second plurality of optical fibers 2515a, 2515b . . . 2515n of optical transmitter 2515 in a circumferential substantially concentric arrangement with respect to the first plurality of optical fibers 2514a, 2514b . . . 2514n. That is, the first plurality of optical transmitters 2514 may be disposed in a first circumferential pattern on the surface 302d and the second plurality of optical transmitters 2515 may be disposed in a second circumferential pattern on the surface 302d that is concentric to the first circumferential pattern of the first plurality of optical transmitters 2514.

Optical fibers 2526a', 2526b' and 2526c' of one or more optical sensors 2526' are disposed substantially at the center of the substantially concentric arrangement of the first and second plurality of optical fibers 2514a, 2514b . . . 2514n and 2515a, 2515b . . . 2515n of optical transmitters 2514 and 2515, respectively. That is, the optical sensor 2526' may be disposed substantially at the center of the concentric arrangement of the first and second circumferential patterns of the optical transmitters 2514 and 2515, respectively.

In view of the light paths 301 and 311 illustrated in FIG. 7A, the optical transmitters 2514, 2515 form multiple light paths in patient tissue distributed substantially radially towards the optical fibers 2526a', 2526b', 2526c' of optical sensor 2526'. The light propagates by reflectance in the patient tissue from the substantially concentric arrangement of the first and second plurality of optical fibers 2514a, 2514b . . . 2514n and 2515a, 2515b . . . 2515n of optical transmitters 2514 and 2515, respectively. The diameters of the optical fibers 2526a', 2526b', 2526c' of optical sensor 2526' may again differ from one another to allow propagation and sensing of light of different wavelengths. The light-emitting electronic devices and photo-electric detectors and electrical cables may be configured as described previously with respect to FIGS. 4A and 4B.

Figure 11:
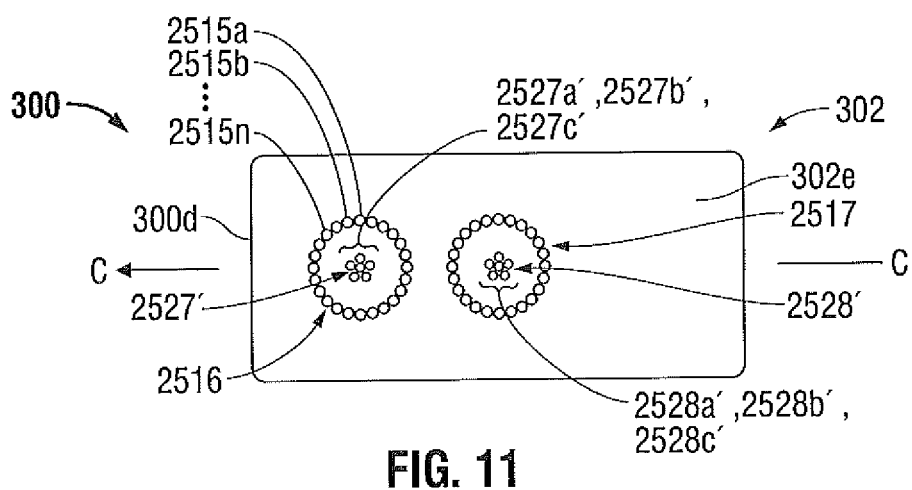
FIG. 11 is a schematic view of another embodiment of an electrically conductive member for use with an electrosurgical instrument according to the present disclosure having two circular arrays of optical transmitters and optical sensors disposed on a surface of the electrically conductive member.

FIG. 11 illustrates yet another embodiment of the electrically conductive member 300 having surface 302. More particularly, electrically conductive member 300e includes two or more optical transmitters, e.g., first optical transmitter 2516 and second optical transmitter 2517, and two or more optical sensors, e.g., first optical sensor 2527' and second optical sensor 2528'. The optical transmitters 2516, 2517 and the optical sensors 2527', 2528' are disposed in a pattern on surface 302e, At least a first plurality of optical fibers 2516a, 2516b . . . 2516n and 2517a, 2517b . . . 2517n form at least a portion of the optical transmitters 2516 and 2517, respectively, and are disposed in a substantially circumferential arrangement.

At least a first plurality of optical fibers 2527a', 2527b', 2527c' and and at least a second plurality of optical fibers 2528a', 2528b', 2528c' form at least a portion of the optical sensors 2527' and 2528', respectively. The first and second plurality of optical fibers 2527a', 2527b', 2527c' and 2528a', 2528b', 2528c' of optical sensors 2527' and 2528', respectively, are disposed substantially at the center of the substantially circumferential arrangement of the first and second plurality of optical fibers 2516a, 2516b . . . 2516n and 2517a, 2517b . . . 2517n that form at least a portion of the optical transmitters 2516 and 2517, respectively, to form a first array of optical transmitting and sensing fibers. The first array of optical transmitter 2516 and optical sensor 2527' is disposed distally with respect to the second array of optical transmitter 2517 and optical sensor 2528'. That is, the first optical sensor 2527' may include fibers 2527a', 2527b', 2527c' that form a first circumferential arrangement and the first optical transmitter 2516 may be disposed substantially at the center of the first circumferential arrangement of the fibers 2527a', 2527b', 2527c'. The second optical sensor 2528' may include fibers 2528a', 2528b', 2528c' that form a second circumferential arrangement and the second optical transmitter 2517 may be disposed substantially at the center of the second circumferential arrangement of the fibers 2528a', 2528b', 2528c'. The second circumferential arrangement may be disposed distally relative to the first circumferential arrangement, along an axis "C" defined through the electrically conductive member 302e.

In view of the light paths 301 and 311 illustrated in FIG. 7A, the optical transmitters 2516, 2517 form multiple light paths in patient tissue distributed substantially radially towards the respective optical fibers 2527a', 2527b', 2527c' of optical sensor 2527' and 2528a', 2528b', 2528c' of optical sensor 2528' in the first and second arrays, respectively. Again, the light propagates by reflectance in the patient tissue. The diameters of the optical fibers 2527a', 2527b', 2527c' of optical sensor 2527' and of optical fibers 2528a', 2528b', 2528c' of optical sensor 2528' may again differ from one another to allow propagation and sensing of light of different wavelengths.

First and second arrays of optical transmitters and optical sensors may also be formed by replacing the concentrically arranged optical fibers 2516a, 2516b . . . 2516n and 2517a, 2517b . . . 2517n of optical transmitters 2516 and 2517, respectively, with optical sensors and by replacing the first and second plurality of optical fibers 2527a', 2527b', 2527c' and 2528a', 2528b', 2528c' of optical sensors 2527' and 2528', respectively, that are disposed substantially at the center of the substantially circumferential arrangement of the first and second plurality of optical fibers 2516a, 2516b . . . 2516n and 2517a, 2517b . . . 2517n with optical transmitters.

Figure 12A:
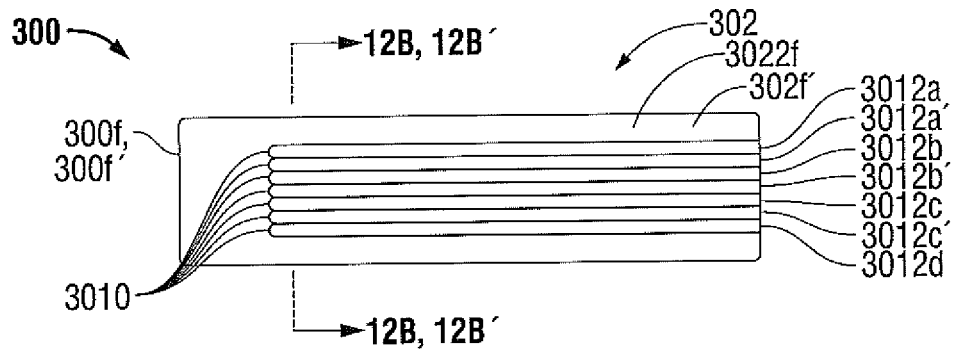
FIG. 12A is a schematic view of a surface of an electrically conductive member for use with an electrosurgical instrument according to the present disclosure having an array of optical transmitters and optical sensors disposed in channels on the surface of the electrically conductive member.
Figure 12B:
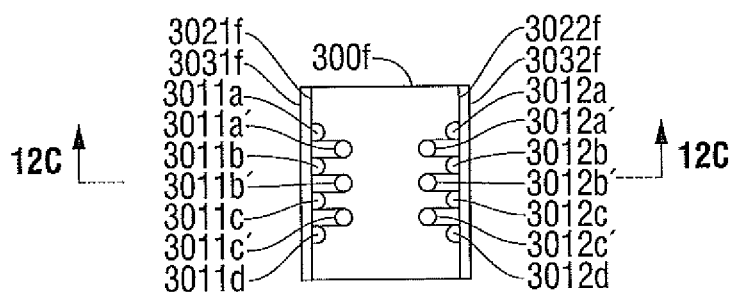
FIG. 12B is an end view of the electrically conductive member of FIG. 12A for an electrosurgical pencil.
Figure 12B:
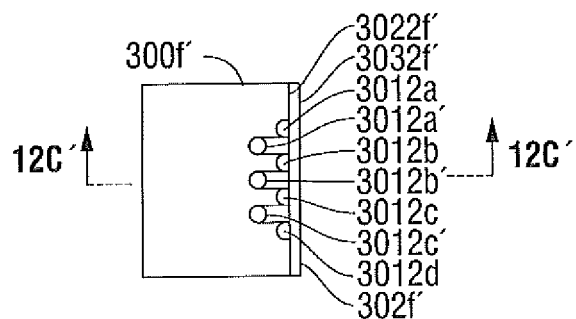

FIGS. 12A, 12B, 12B', 12C, 12C' and 13 illustrate different embodiments of yet another electrically conductive member 300 for use with an electrosurgical instrument having a surface 302 according to the present disclosure. More particularly, FIGS. 12A, 12B, 12C and 13 illustrate an electrically conductive member 300f having at least a first lateral surface 3021f and a second lateral surface 3022f on an opposing side of the electrically conductive member 300f.

The electrically conductive member 300f includes on first and second lateral surfaces 3021f and 3022f one or more optical transmitters, e.g., optical transmitters 3011a, 3011b, 3011c, 3011d and 3012a, 3012b, 3012c, 3012d. The electrically conductive member 300f also includes on first and second lateral surfaces 3021f and 3022f one or more optical sensors, e.g., optical sensors 3011a', 3011b', 3011c' and 3012a', 3012b', 3012c'. The optical transmitters 3011a, 3011b, 3011c, 3011d and 3012a, 3012b, 3012c, 3012d and optical sensors 3011a', 3011b', 3011c' and 3012a', 3012b', 3012c' each may include an optical fiber having at least one end 3010 with a tapered configuration to function as a prism. That is, the optical transmitters 3011a, 3011b, 3011c, 3011d and 3012a, 3012b, 3012c, 3012d may each have tapered end 3010 that forms a prism.

Figure 12C:
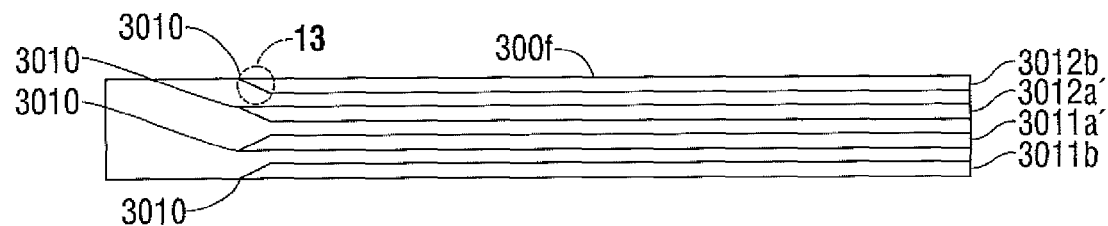
FIG. 12C is a schematic view of the electrically conductive member of FIG. 12B taken along section line 12C-12C.
Figure 12C:
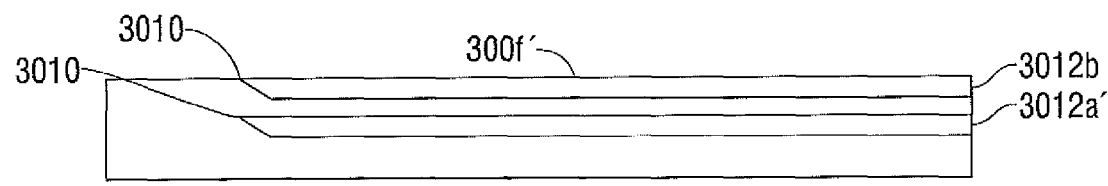
Figure 13:
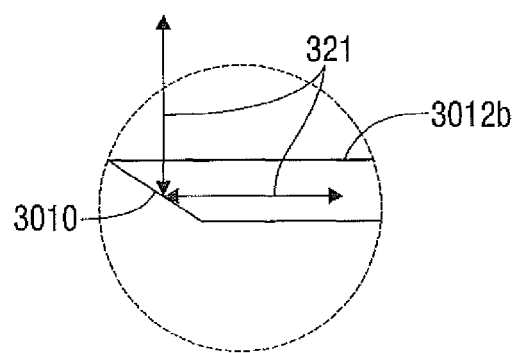
FIG. 13 is an enlarged view of an end of an optical fiber illustrated in FIG. 12C'.

As illustrated in FIGS. 12B and 12C, the optical sensors 3011a', 3011b', 3011c' and 3012a', 3012b', 3012c' are each positioned in channels (for simplicity, the channels are not separately numbered) in the respective surfaces 3021f and 3022f having a depth within the electrically conductive member 300f that is greater than the depth of channels (for simplicity, the channels are not separately numbered) within which optical transmitters 3011a, 3011b, 3011c, 3011d and 3012a, 3012b, 3012c, 3012d are positioned.

The tapered configuration ends 3010 of the optical transmitters 3011a, 3011b, 3011c, 3011d and 3012a, 3012b, 3012c, 3012d are positioned within the respective surfaces 3021f and 3022f to transmit light through patient tissue via the tapered configuration ends 3010. Similarly, the tapered configuration ends 3010 of the optical sensors 3011a', 3011b', 3011c' and 3012a', 3012b', 3012c' are positioned within the respective surfaces 3021f and 3022f to sense light propagating by reflectance, through patient tissue via the tapered configuration ends 3010. For simplicity, light 321 is identified in FIG. 13 as reflecting in either direction to represent the two different functions of transmission into the patient tissue and sensing by reflectance from the patient tissue. The light 321 propagates and reflects through patient tissue. The first and second lateral surfaces 3021f, 3022f may each include translucent heat-insulating layers 3031f and 3032f to cover the respective channels and the optical fibers positioned therewithin.

The electrically conductive member 300f illustrated in FIGS. 12A, 12B, 12C and 13, which includes the optical transmitters and optical sensors in both the first and second lateral surfaces 3021f, 3022f may be adapted as a blade for an electrosurgical pencil in a similar manner as described previously with respect to FIGS. 1 through 6b.

The electrically conductive member 300f illustrated in FIGS. 12A, 12B', 12C' and 13 is configured identically to the electrically conductive member 300f except that only the optical transmitters 3012a, 3012b, 3012c, 3012d and optical sensors 3012a', 3012b', 3012c' associated with second lateral surface 3022f and their respective channels (again not numbered for simplicity) are illustrated. The electrically conductive member 300f' may be adapted as a jaw member of a bipolar electrosurgical forceps, as described in more detail below with respect to FIG. 14.

Figure 14:
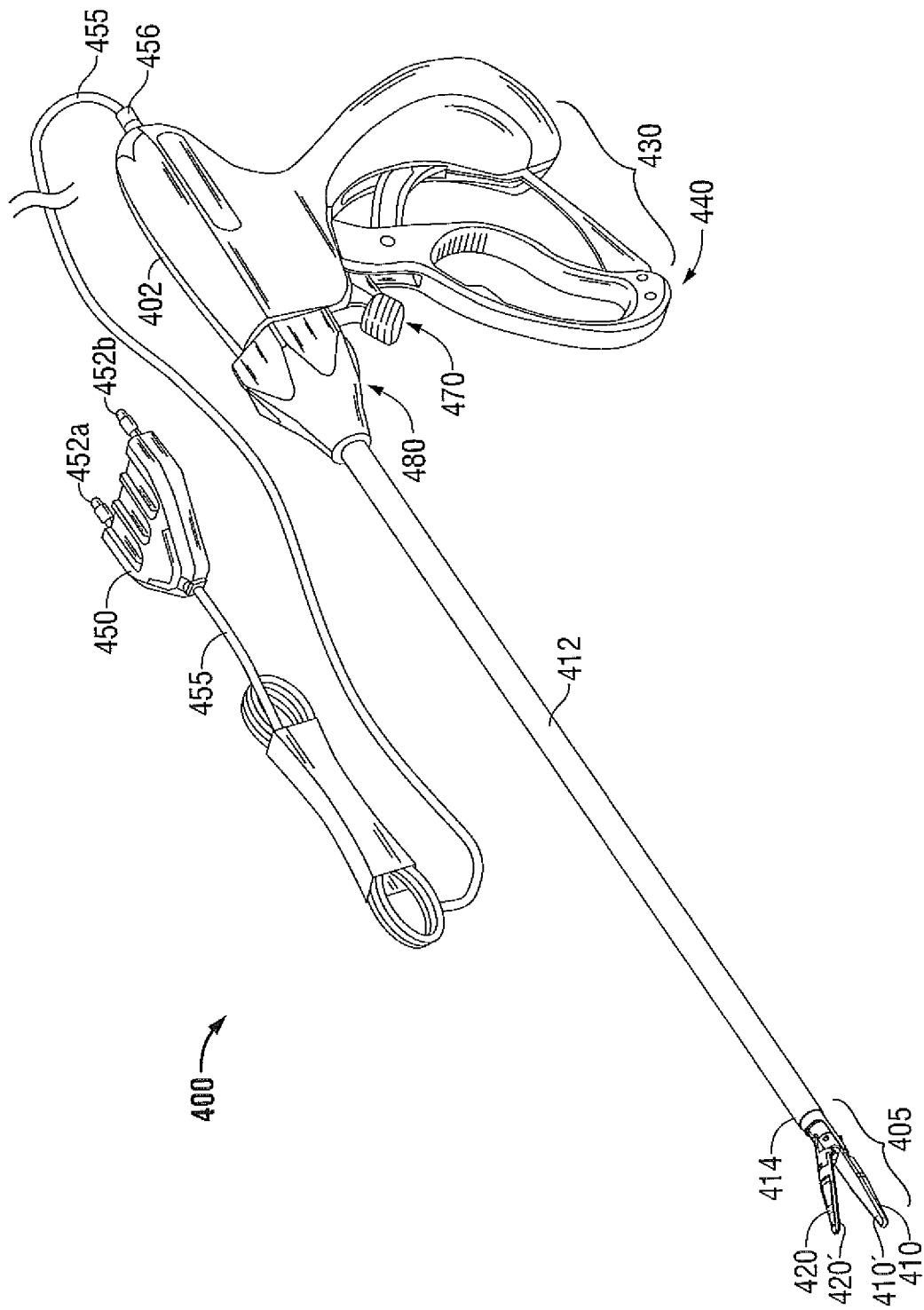
FIG. 14 is a perspective view of a bipolar electrosurgical forceps according to the present disclosure illustrating one embodiment of an end effector assembly having an optical transmitter positioned to propagate light through patient tissue and optical sensors positioned to sense light propagating through patient tissue for monitoring hydration levels in tissue during operation of the bipolar forceps.

FIG. 14 illustrates a bipolar electrosurgical forceps 400 according to the present disclosure illustrating one embodiment of an end effector assembly 405 having an optical transmitter positioned to propagate light through patient tissue and optical sensors positioned to sense at least a portion of the light propagating through the patient tissue for monitoring hydration levels in tissue during operation of the bipolar forceps.

One embodiment of a bipolar forceps 400 is shown for use with various surgical procedures and generally includes a housing 402, a handle assembly 430, a rotating assembly 480, a trigger assembly 470 and an end effector assembly 405 which mutually cooperate to grasp, seal and divide tubular vessels and vascular tissue.

End effector assembly 405 is attached to distal end 414 of shaft 412 and includes a pair of opposing jaw members 410 and 420. Movable handle 440 of handle assembly 430 is ultimately connected to a drive rod (not shown) disposed within the shaft 412 which, together, mechanically cooperate to impart movement of the jaw members 410 and 420 from an open position wherein the jaw members 410 and 420 are disposed in spaced relation relative to one another, to a clamping or closed position wherein the jaw members 410 and 420 cooperate to grasp tissue.

Forceps 400 also includes an electrical interface or plug 450 which connects the forceps 400 to a source of electrosurgical energy, e.g., a generator (not shown). Plug 450 includes a pair of prong members 452a and 452b that are dimensioned to mechanically and electrically connect the forceps 400 to the source of electrosurgical energy. An electrical cable 455 extends from the plug 450 to a sleeve 456 which securely connects the cable 455 to the forceps 400.

The first and second jaw members 410 and 420 each have respective inwardly facing surfaces 410' and 420' associated therewith. As defined herein, the inwardly facing surfaces 410' and 420' may be formed partially of an electrically conductive material and partially of an electrically insulating material. The electrically conductive material is in electrical communication with the source of electrosurgical energy. Consequently, the inwardly facing surfaces 410' and 420' may be referred to as electrically conductive surfaces 410', 420' and as electrically insulating surfaces 410', 420'.

The first and second jaw members 410 and 420 respectively are each adapted for relative movement between an open position to receive tissue and a closed position engaging tissue between the inwardly facing surfaces 410' and 410'. That is, first and second jaw members 410 and 420 are disposed in pivotal relationship with respect to one another and attached to distal end 414 of at least one shaft, e.g., shaft 412. Each jaw member 410 and 420 supports an electrically conductive surface 410' and 420', respectively, thereon. Jaw member 410 and/or jaw member 420 is configured to be connected to the source of electrosurgical energy (via the plug 450), One of the jaw members, e.g., lower jaw member 410, may be in a fixed position with respect to the shaft 412. The jaw members 410 and 420 of end effector assembly 405 are configured to effect optical transmission of light through patient tissue.

Figure 14A:
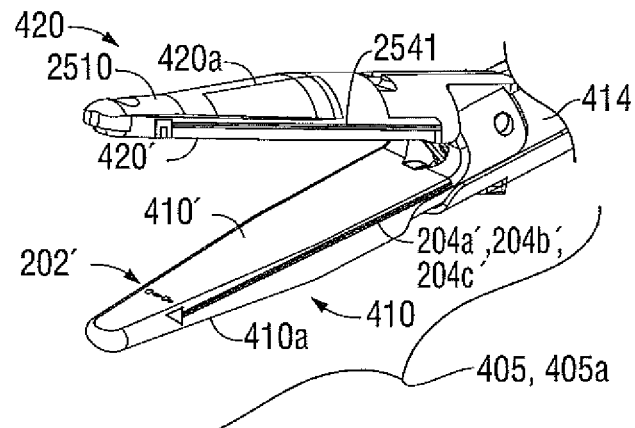
FIG. 14A is an enlarged perspective view of the embodiment of the jaw members of the end effector assembly of FIG. 14.

FIG. 14A illustrates one embodiment of end effector assembly 405. More particularly, end effector assembly 405a includes one of the jaw members 410 and/or 420, e.g., upper jaw member 420a, configured with one or more optical transmitters, e.g., optical transmitter 2510, as described previously with respect to FIG. 4A, that is positioned in the surface 420' to propagate light through patient tissue.

One or both of the jaw members, e.g., lower jaw member 410a, may be configured with one or more optical sensors, e.g., optical sensor 202', as described previously with respect to FIG. 2B with the exception that the large diameter single optical fiber 208 is replaced by a plurality of optical fibers such as optical fibers 204a', 204b', 204c' having diameters that differ from one another. Optical sensor 202' is positioned to sense at least a portion of the light (not shown) propagating through the patient tissue. The light is transmitted by the optical transmitter 2510 positioned in the upper jaw member 420a, for monitoring hydration levels in the patient tissue during operation of the electrosurgical forceps 400.

As described below with respect to FIGS. 19-20, one or both of the jaw members 410 and 420 is disposed in optical communication with a light source 7321, 7322 and/or 7323 and the other of the jaw members 410 and 420 is disposed in optical communication with a light sensor 7341 and/or 7342 for monitoring hydration levels in the tissue 2 during operation of the electrosurgical forceps 400.

Figure 14B:
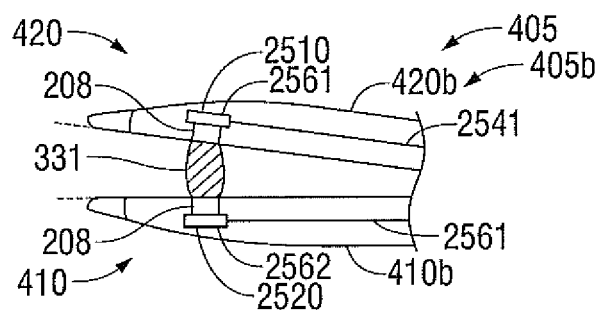
FIG. 14B is a profile view of another embodiment of the jaw members of the end effector assembly of FIG. 14.

FIG. 14B illustrates another embodiment of the end effector assembly 405 of FIG. 14. More particularly, end effector assembly 405b includes one of the jaw members 410 and/or 420, e.g., upper jaw member 420b, configured with one or more optical transmitters, e.g., optical transmitter 2510 that includes a light-emitting electronic device (as described previously with respect to FIG. 4A) that is positioned in the surface 420' to propagate light through patient tissue.

One or both of the jaw members, e.g., lower jaw member 410b, is configured with one or more optical sensors, e.g., optical sensor 2520 that includes a photo-electric detector (as described previously with respect to FIG. 4B) that is positioned to sense at least a portion of light 331 propagating through the patient tissue. The light 331 is transmitted by the optical transmitter 2510 positioned in the upper jaw member 420, for monitoring hydration levels in the patient tissue during operation of the electrosurgical forceps 400.

As described below with respect to FIGS. 19-20, one or both of the jaw members 410 and 420 is disposed in optical communication with a light source 7321, 7322 and/or 7323 and the other of the jaw members 410 and 420 is disposed in optical communication with a light sensor 7341 and/or 7342 for monitoring hydration levels in the tissue 2 during operation of the electrosurgical forceps 400.

Figure 14C:
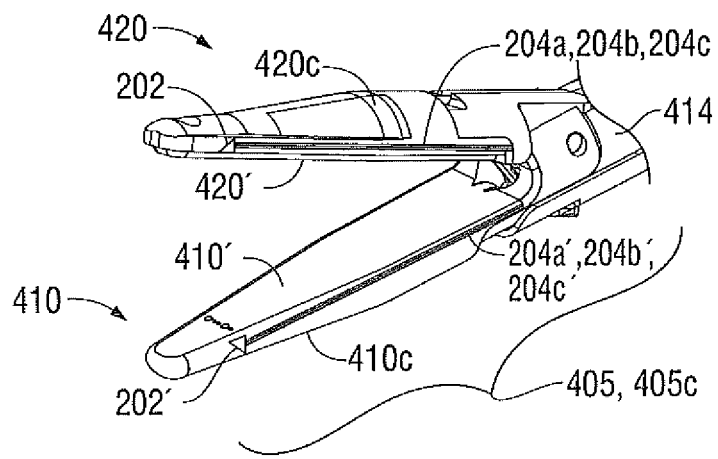
FIG. 14C is an enlarged perspective view of another embodiment of the jaw members of the end effector assembly of FIG. 14.

FIG. 14C illustrates still another embodiment of the end effector assembly 405 of FIG. 14. More particularly, end effector assembly 405c includes one or more jaw members 410 and/or 420, e.g., upper jaw member 420c, configured with one or more optical transmitters, e.g., optical transmitter 202, as described previously with respect to FIG. 4A with the exception that the large diameter single optical fiber 208 is replaced by a plurality of optical fibers such as optical fibers 204a, 204b, 204c having diameters that differ from one another. The optical transmitter 202 is positioned in the surface 420' to propagate light through patient tissue.

One or both of the jaw members, e.g., lower jaw member 410b, is configured with one or more optical sensors, e.g., optical sensor 202', as described previously with respect to FIG. 3B with the exception that the large diameter single optical fiber 208 is replaced by a plurality of optical fibers such as optical fibers 204a', 204b', 204c' having diameters that differ from one another. The optical sensor 202' is positioned to sense at least a portion of light propagating through the patient tissue. The light has been transmitted by the optical transmitter 202 positioned in the upper jaw member 420, for monitoring hydration levels in the patient tissue during operation of the electrosurgical forceps 400.

Again, as described below with respect to FIGS. 19-20, at least one of the jaw members 410 and 420 is disposed in optical communication with a light source 7321, 7322 and/or 7323 and the other of the jaw members 410 and 420 is disposed in optical communication with a light sensor 7341 and/or 7342 for monitoring hydration levels in the tissue 2 during operation of the electrosurgical forceps 400.

Figure 15A:
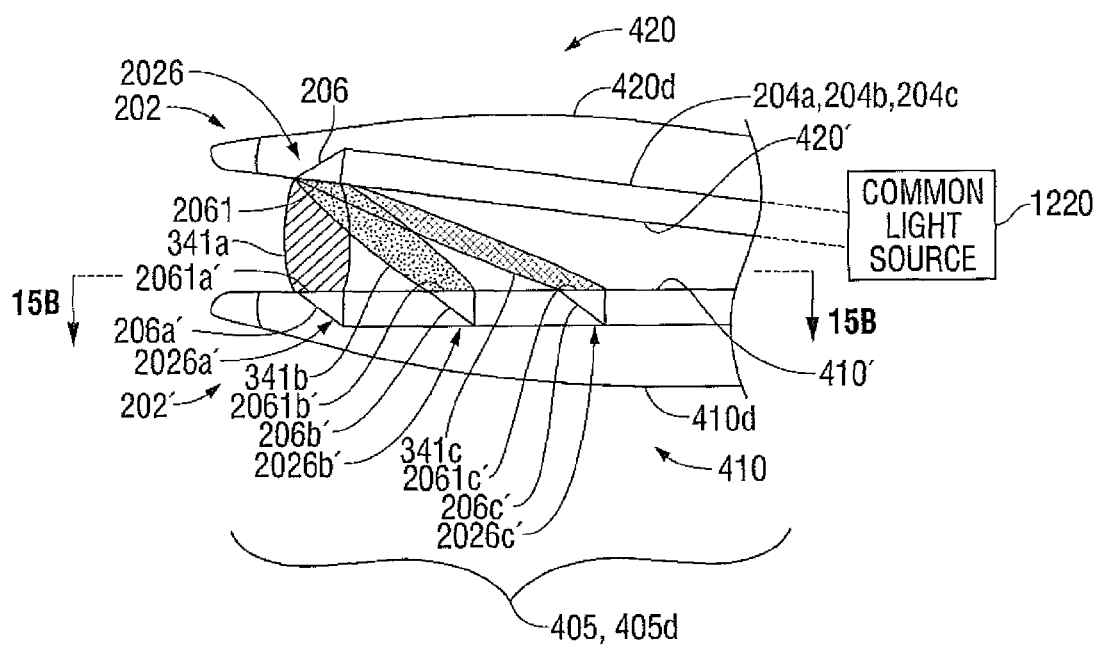
FIG. 15A is a schematic, side view of another embodiment of the jaw members of the end effector assembly of FIG. 14.
Figure 15B:
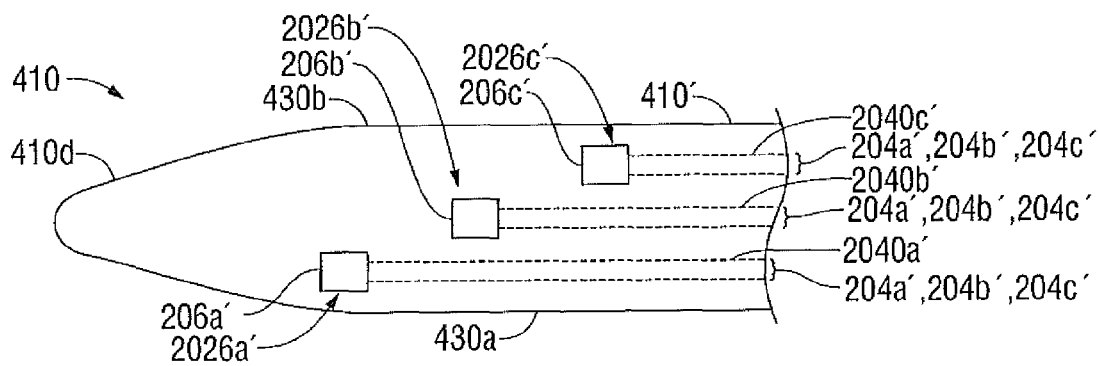
FIG. 15B is a schematic, view of the lower jaw member of the end effector assembly of FIG. 15A taken along section line 15B-15B.

FIGS. 15A and 15B illustrate yet another embodiment of the end effector assembly 405 of FIG. 14. More particularly, end effector assembly 405d includes the jaw members 410 and/or 420, e.g., upper jaw member 420d, configured with one or more optical transmitters 2026, e.g., optical transmitter 202, as described previously with respect to FIG. 3A with the exception that the large diameter single optical fiber 208 is omitted and one surface 2061 of prism 206 is exposed directly on inwardly facing surface 420' to reflect light from a common light source 1220 via the prism 206 to patient tissue (not shown). Thus, optical transmitter 2026 is positioned in the inwardly facing surface 420' to propagate light in different paths, e.g., light paths 341a, 341b, 341c, through patient tissue.

One or both of the jaw members, e.g., lower jaw member 410d, is configured with one or more optical sensors, e.g., first, second and third optical sensors 2026a', 2026b', 2026c', respectively, that are similar to optical sensor 202', as described previously with respect to FIG. 3B with the exception that the large diameter single optical fiber 208 is again omitted and one surface 2061a', 2061b', 2061c' of prisms 206a', 206b', 206c', respectively, is exposed directly on inwardly facing surface 410' to reflect light via the prism 206 from patient tissue (not shown) through a plurality of optical fibers 204a', 204b', 204c' that are routed through individual channels in channel groups 2040a', 2040b', 2040c', respectively.

The optical sensors 2026a', 2026b', 2026c' are each positioned to sense at least a portion of the light propagating in light paths 341a, 341b, 341c, respectively, through the patient tissue. The light is transmitted by the optical transmitter 2026 positioned in the upper jaw member 420, for monitoring hydration levels in the patient tissue during operation of the electrosurgical forceps 400. To enable routing of the optical fibers 204a', 204b', 204c' in channel groups 2040a', 2040b', 2040c', the channel groups 2040a', 2040b', 2040c' are formed laterally offset from one another within the lower jaw member 410d. More particularly, as indicated above, the first, second and third optical sensors 2026a', 2026b', 2026c' each have a prism associated therewith, e.g., prisms 206a', 206b', 206c', respectively, mounted on the fixed jaw member 410d. The first prism 206a' is mounted distally of the second prism 206b' and the second prism 206b' is mounted distally of the third prism 206c'. The first prism 206a' is mounted proximal to first lateral edge 430a of the surface 410d. The second prism 206b' is laterally offset with respect to the first prism 206a' and is further laterally offset with respect to the lateral edge 430a. The third prism 206c' is laterally offset with respect to both first and second prisms 206a' and 206b', respectively, and may be proximal to second lateral edge 430b of the surface 410d.

Correspondingly, the first channel group 2040a' is laterally offset from the second channel group 2040b' and both the first and second channel groups 2040a' and 2040b are laterally offset from third channel group 2040c'.

As described below with respect to FIGS. 19-20, one or both of the jaw members 410 and 420 may be disposed in optical communication with a light source 7321, 7322 and/or 7323 and the other of the jaw members 410 and 420 may be disposed in optical communication with a light sensor 7341 and/or 7342 for monitoring hydration levels in the tissue 2 during operation of the electrosurgical forceps 400.

Figure 15C:
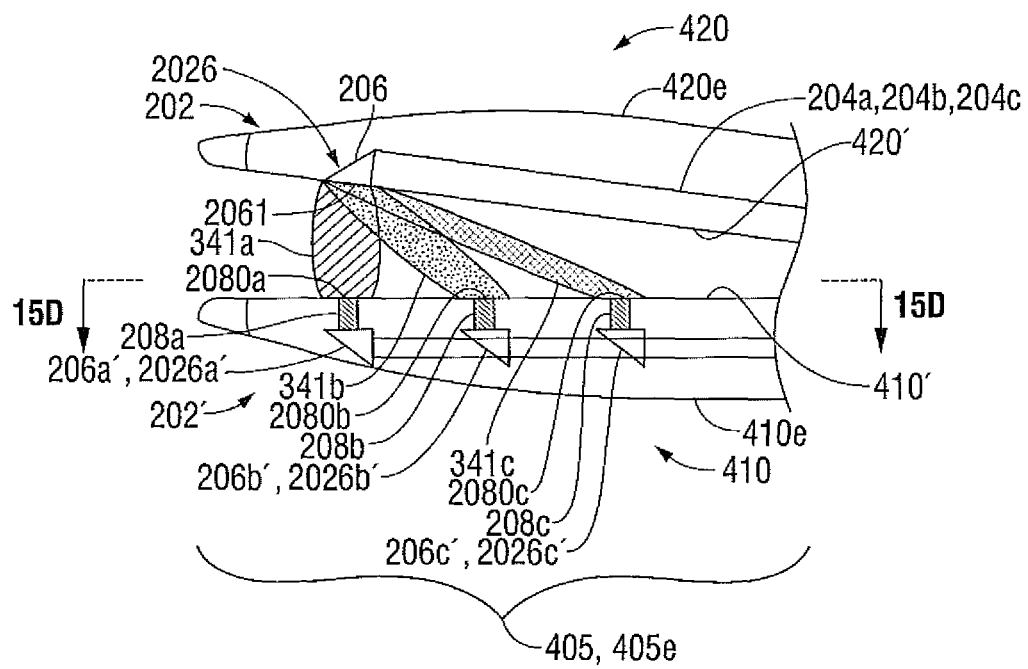
FIG. 15C is a schematic, side view of another embodiment of the jaw members of the end effector assembly of FIG. 14.
Figure 15D:
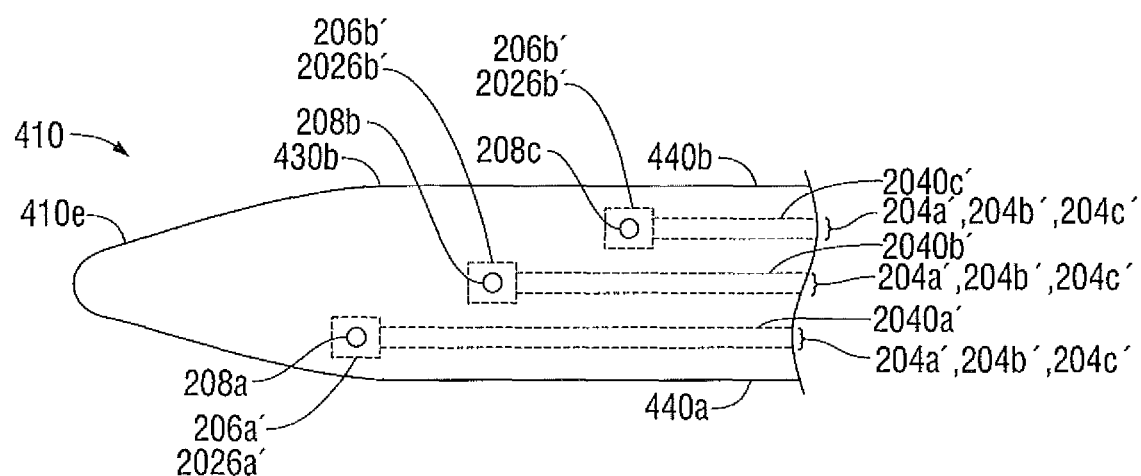
FIG. 15D is a schematic view of the lower jaw member of the end effector assembly of FIG. 15C taken along section line 15D-15D.

FIGS. 15C and 15D illustrate yet another embodiment of the end effector assembly 405 of FIG. 14 having lower and upper jaw members 410 and 420, respectively. More particularly, end effector assembly 405e includes upper jaw member 420e that is identical to upper jaw member 420d as described above with respect to FIGS. 15A and 15D. The jaw members, e.g., lower jaw member 410e, may be substantially identical to lower jaw member 410d described above with respect to FIGS. 15A and 15B. Lower jaw member 410e is also configured with one or more optical sensors, e.g., first, second and third optical sensors 2026a', 2026b', 2026c', respectively, that are again similar to optical sensor 202', as described previously with respect to FIG. 4B with the exception that the large diameter single optical fiber 208 is now included.

As illustrated in FIGS. 15C and 15D, one end 2080a, 2080b, 2080c of each large diameter single optical fiber 208a, 208b, 208c, respectively, is exposed directly on inwardly facing surface 410' to sense light propagating in light paths 341a, 341b, 341c, respectively, from patient tissue (not shown) and to communicate the light to be reflected via the respective prisms 206a', 206b', 206c' again through a plurality of optical fibers 204a', 204b', 204c' that are routed through individual channels in channel groups 2040a', 2040b', 2040c', respectively.

In a similar manner as with respect to end effector assembly 405d described with respect to FIGS. 15A and 15C, the optical sensors 2026a', 2026b', 2026c' are each positioned to sense at least a portion of the light propagating in light paths 341a, 341b, 341c, respectively, through the patient tissue. The light is transmitted by the optical transmitter 2026 positioned in the upper jaw member 420, for monitoring hydration levels in the patient tissue during operation of the electrosurgical forceps 400. To enable routing of the optical fibers 204a', 204b', 204c' in channel groups 2040a', 2040b', 2040c', the channel groups 2040a', 2040b', 2040c' are formed laterally offset from one another within the lower jaw member 410d. More particularly, as indicated above, the first, second and third optical sensors 2026a', 2026b', 2026c' each have a large diameter single optical fiber 208a, 208b, 208c associated with prisms 206a', 206b', 206c', respectively, that are mounted within the fixed jaw member 410e. The first large diameter single optical fiber 208a and associated prism 206a' are mounted distally of the second large diameter single optical fiber 208b and associated second prism 206b', and the second large diameter single optical fiber 208b and associated second prism 206b' are mounted distally of the third large diameter single optical fiber 208c and associated prism 206c'.

The first optical fiber 208a and associated first prism 206a' may be mounted in proximity to first lateral edge 440a of the surface 410e, The second optical fiber 208b and associated first prism 206b' may be laterally offset with respect to the first optical fiber 208a and associated first prism 206a' and may be further laterally offset with respect to the first lateral edge 440a. The third optical fiber 208c and associated third prism 206c' may be laterally offset with respect to both first and second optical fiber 208a, 208b and associated prisms 206a' and 206b', respectively, and may be in proximity to second lateral edge 440b of the surface 410e.

Correspondingly, the first channel group 2040a' is laterally offset from the second channel group 2040b' and both the first and second channel groups 2040a' and 2040b are laterally offset from third channel group 2040c'.

The first jaw member 410e is thus a compound jaw member in which the first, second and third optical fibers 208a, 208b, 208c, respectively, extend partially into a secondary region 410e' defined within the first jaw member 410e away from the surface 410'. Additionally, the first, second and third prisms 206a', 206b', 206c' and the optical fibers 204a', 204b', 204c' and channel groups 2040a', 2040b', 2040c' are mounted predominantly, if not entirely, within the secondary region 410e'.

FIGS. 16, 16A, 17 and 18 illustrate various embodiments of an end effector assembly 505 according to the present disclosure for a parallel jaw type bipolar electrosurgical forceps (not shown) having first and second jaw members 510 and 520 having one or more optical transmitters positioned to propagate light through patient tissue and one or more optical sensors positioned to sense at least a portion of the light propagating through the patient tissue for monitoring hydration levels in tissue during operation of the bipolar forceps. The end effector assembly 505 ay be configured such that the jaw members 510 and 520 remain substantially parallel to one another during the relative movement between the open position to the closed position and vice versa. One of the jaw members 510 or 520 may be in a fixed position with respect to a shaft (not shown). Alternatively, both of the jaw members 510 and 520 may be movable with respect to a shaft (not shown).

Figure 16:
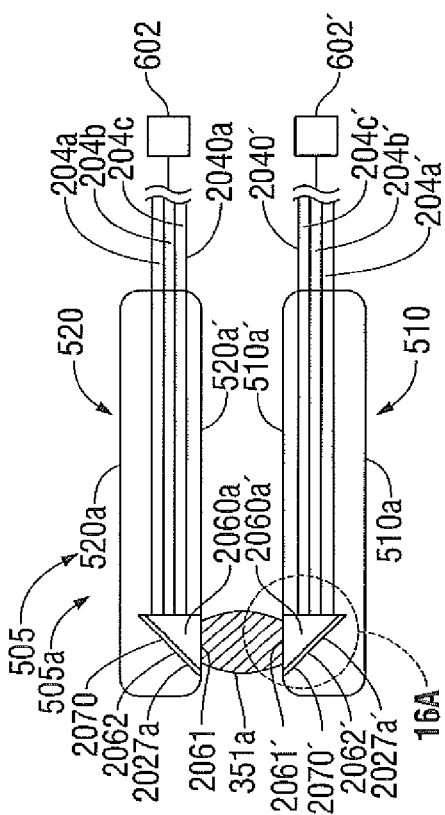
FIG. 16 is a schematic, side view of another embodiment of an end effector assembly according to the present disclosure for a parallel jaw type bipolar electrosurgical forceps assembly having an optical transmitter positioned to propagate light through patient tissue and optical sensors positioned to sense light propagating through patient tissue for monitoring hydration levels in tissue during operation of the bipolar forceps.
Figure 16A:
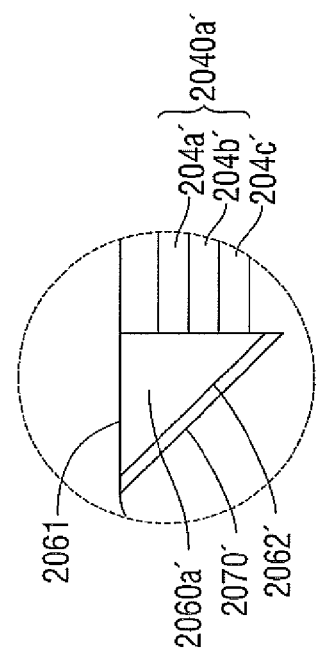
FIG. 16A is an enlarged view of the area of detail 16A illustrated in FIG. 16.

More particularly, referring first to FIGS. 16 and 16A, end effector assembly 505a includes first jaw member 510a and second jaw member 520a having respective inwardly facing surfaces 510a' and 520a' associated therewith. The jaw members 510a and 520a are adapted for relative movement between an open position to receive tissue and a closed position engaging tissue between the inwardly facing surfaces 510a' and 520a'.

In a similar manner as with respect to jaw members 410 and 420 discussed previously with respect to FIGS. 14A to 15D, the inwardly facing surfaces 510a' and 520a' of each jaw member 510a and 520a, respectively, is formed partially of an electrically conductive surface and of an electrically insulating surface. One or both of the jaw members 510a and/or 520a is configured to be connected to a source of electrosurgical energy (not shown). One of the jaw members may be in a fixed position with respect to a shaft (not shown).

One or both of the jaw members, e.g., jaw member 520a, may be configured with one or more optical transmitters, e.g., optical transmitter 2027a that is similar to optical transmitter 202 described previously with respect to FIG. 3A, except that optical transmitter 2027a does not include large diameter optical fiber 208. The optical transmitter 2027a includes prism 2060a having surface 2061 that is exposed on inwardly facing surface 520a'. The optical transmitter 2027 and associated prism 2060a and surface 2061 are positioned to propagate light through patient tissue (not shown) in a light path 351a.

Similarly, one of the jaw members, e.g., jaw member 510a, may be configured with one or more optical sensors, e.g., optical sensor 2027a' that is similar to optical sensor 202' described previously with respect to FIG. 3B, except that optical sensor 2027a' also does not include large diameter optical fiber 208. The optical sensor 2027a' includes prism 2060a' having surface 2061' that is exposed on inwardly facing surface 510a'. The optical sensor 2027a' and associated prism 2060a' and surface 2061' are positioned to sense at least a portion of the light propagating via light path 351a through the patient tissue for monitoring hydration levels in tissue during operation of the electrosurgical forceps.

The light reflected via the respective prisms 2027a and 2027a' propagates through plurality of optical fibers 204a, 204b, 204c and 204a', 204b', 204c' that are routed through individual channels in channel groups 2040a and 2040a' in jaw members 520a and 510a, respectively. The optical fibers 204a, 204b, 204c and 204a', 204b', 204c' again have diameters that differ from one another. The optical fibers 204a, 204b, 204c and 204a', 204b', 204c' are routed in individual channels to reduce interference between one another.

The optical transmitter 2027a receives light propagating through channel group 2040a from a light source 602 that is in optical-electrical communication therewith, while optical sensor 2027a' propagates light through channel group 2040a' that is in optical-electrical communication with a light detector 602'.

As illustrated in more detail in FIG. 16A, the prisms 2027a and 2027a' may include angled surfaces 2062 and 2062' with reflective coatings 2070 and 2070', respectively, to increase the efficiency of the reflection of light via the prisms.

Figure 17:
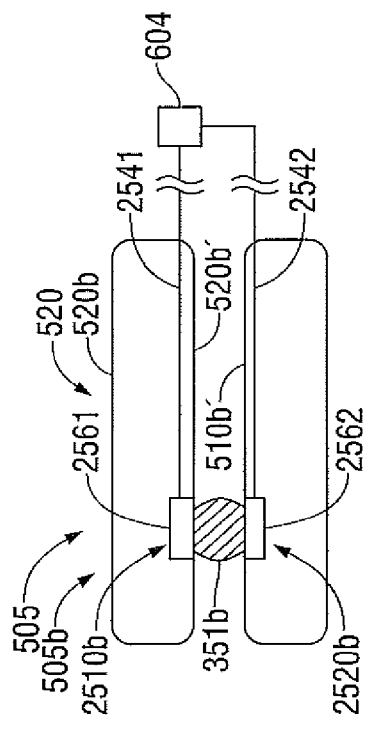
FIG. 17 is a schematic, side view of another embodiment of the parallel jaw type bipolar electrosurgical forceps assembly of FIG. 16 having an optical transmitter positioned to propagate light through patient tissue and optical sensors positioned to sense light propagating through patient tissue for monitoring hydration levels in tissue during operation of the bipolar forceps.

FIG. 17 illustrates another embodiment of end effector assembly 505 according to the present disclosure for a parallel jaw type bipolar electrosurgical forceps (not shown) having first and second jaw members 510 and 520.

In a similar manner as with respect to end effector assembly 505a described above with respect to FIGS. 16 and 16A, jaw members 510b and 520b of end effector assembly 505b include, respectively, inwardly facing surfaces 510b' and 520b'.

Jaw members 510b and 520b differ from jaw members 510a and 520a in that in place of optical transmitter 2027a and optical sensor 2027a, respectively, second jaw member 520b includes optical transmitter 2510b that is similar to optical transmitter 2510 having light-emitting electronic device 2561 and electric cable 2541 described above with respect to FIG. 4A, except that optical transmitter 2510b does not include large diameter optical fiber 208. Optical transmitter 2027b is in electrical communication with a processor 600.

Similarly, first jaw member 510b includes optical sensor 2520b that is similar to optical sensor 2520 having photoelectric detector 2562 and electrical cable 2542 described above with respect to FIG. 4B, except that optical sensor 2520b also does not include large diameter optical fiber 208.

The optical transmitter 2510b and optical sensor 2520b are in electrical communication, via electrical cables 2541 and 2542, respectively, with a processor 604.

Optical transmitter 2027b may propagate light from second surface 520b' in a path 351b through patient tissue (not shown) to optical sensor 2027b' and that the propagation and intensity of the light may be controlled by the processor 604.

Figure 18:
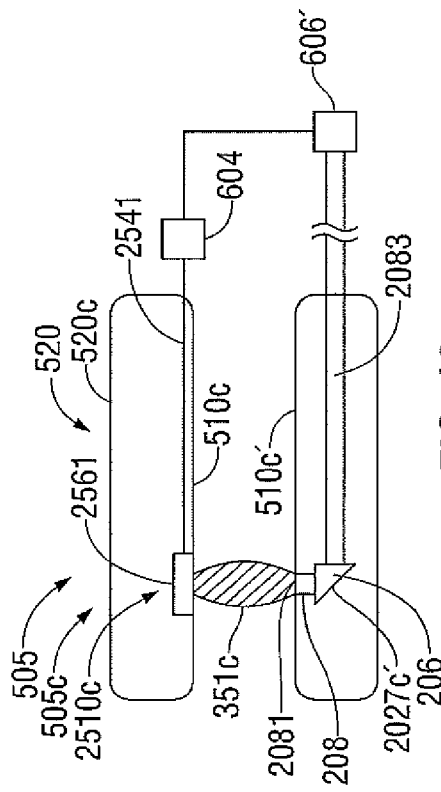
FIG. 18 is a schematic, side view of yet another embodiment of the parallel jaw type bipolar electrosurgical forceps assembly of FIG. 16 having an optical transmitter positioned to propagate light through patient tissue and optical sensors positioned to sense light propagating through patient tissue for monitoring hydration levels in tissue during operation of the bipolar forceps.

FIG. 18 illustrates yet another embodiment of end effector assembly 505 according to the present disclosure for a parallel jaw type bipolar electrosurgical forceps (not shown) having first and second jaw members 510 and 520.

In a similar manner as with respect to end effector assemblies 505a and 505b described above with respect to FIGS. 16, 16A and 17, jaw members 510c and 520c of end effector assembly 505c include, respectively, inwardly facing surfaces 510c' and 520c'. Second jaw member 520c includes optical transmitter 2510c that is identical to optical transmitter 2510b illustrated in FIG. 17 and includes light-emitting electronic device 2561 and electrical cable 2541.

However, in contrast to first jaw member 510b illustrated in FIG. 16, first jaw member 510c includes optical sensor 2027c' which is similar to optical sensor 202' described above with respect to FIG. 3B, and which includes large diameter optical fiber 208 having one end 2081 exposed on surface 510c' and which is in optical communication with prism 206 that is included in optical sensor 2027c'. Additionally, optical sensor 2027c' differs from optical sensor 2027a' illustrated in FIGS. 16 and 16A in that in place of the plurality of optical fibers 204a', 204b', 204c' in optical communication with the prism 2060a', optical sensor 2027c' includes a large diameter optical fiber 2083 that is in optical communication with the prism 206 such that light emitted by optical transmitter 2510c propagates in light path 351c to be sensed at end 2081 of optical fiber 208 exposed on surface 510c'. The light propagates in light path 351c through large diameter optical fiber 208 to prism 206 where it is reflected to propagate through large diameter optical fiber 2083 to a photo-detector 606'.

The photo-detector 606' is in communication with the processor 604. Similarly, the processor 604 is in communication with the light-emitting electronic device 2510c of optical transmitter 2510c via the electrical cable 2541. Optical transmitter 2510c may propagate light from second surface 520c' in path 351c through patient tissue (not shown) to optical sensor 2520b and that the propagation and intensity of the light may be controlled by the processor 604.

Figure 19:
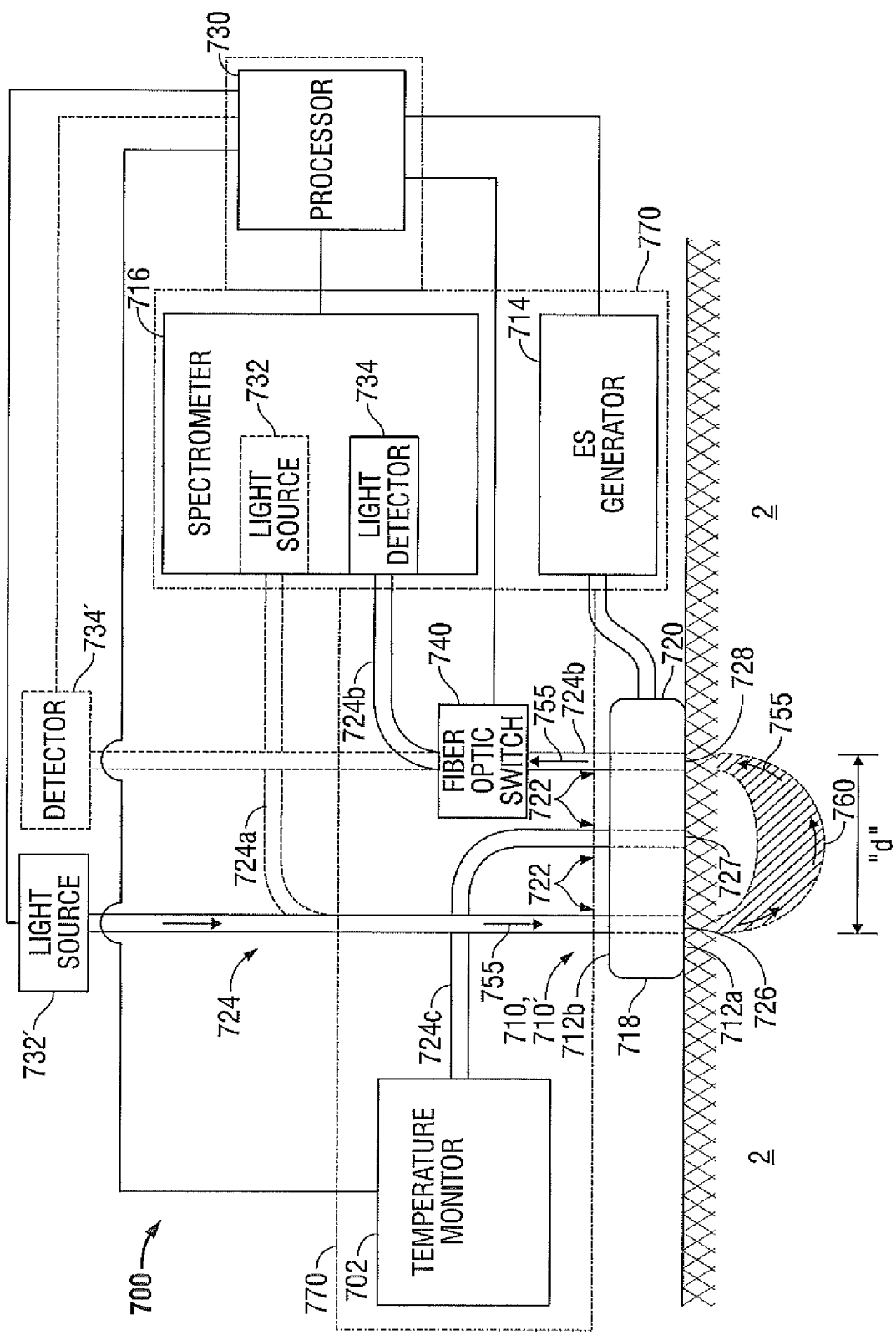
FIG. 19 is a schematic view of a system for monitoring water displacement during treatment of patient tissue according to the present disclosure.
Figure 20:
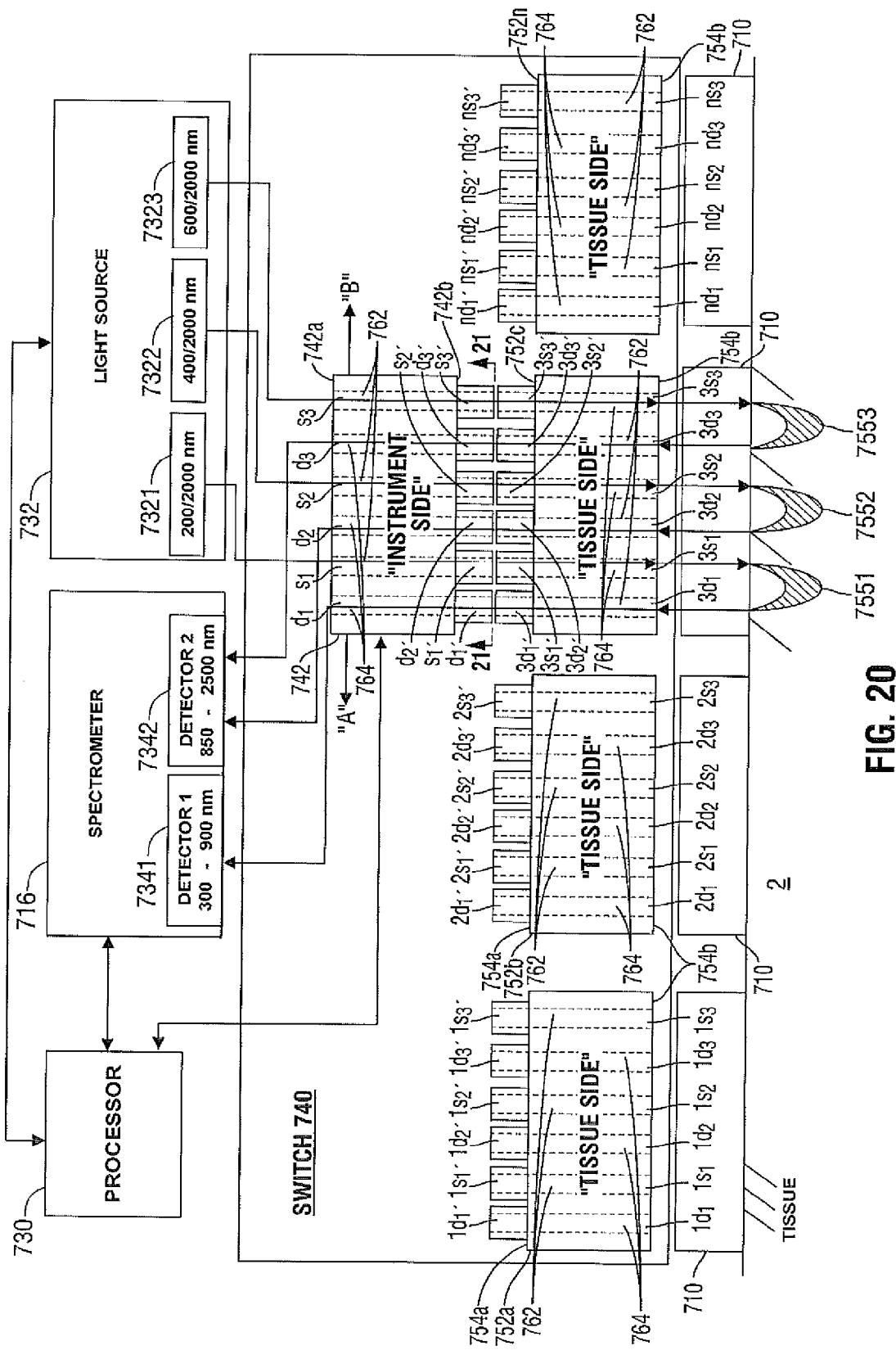
FIG. 20 is a schematic view of one embodiment of the mechanical-optical multiplexer switch included within the system for monitoring water displacement of FIG. 19 as configured with respect to the array of optical transmitters and optical sensors illustrated in FIG. 11.

Turning now to FIGS. 19-20, there is illustrated one embodiment of an optical hydrology system 700 according to the present disclosure that includes schematically an exemplary embodiment of an optical hydrology array 710 according to the present disclosure. Optical hydrology array 710 is formed, in one embodiment, in a flat rectangular plate type arrangement. The array 710 includes a first or lower surface 712a that is configured in a generally flat shape suitable to be disposed in proximity to patient tissue 2 (see FIG. 19). A second or upper surface 712b is disposed in a position opposite to the first or lower surface 712a. First and second side walls 718 and 720, respectively, straddle between the first and second surfaces 712a and 712b, respectively to form the generally box-like flat rectangular plate type configuration of the array 710 for housing the optical components therein.

The array 710 further includes a plurality of apertures 722 that extend from the first surface 712a to the second surface 712b. The plurality of apertures 722 penetrate through the first and second surfaces 712a and 712b, respectively, and are configured in a matrix-like arrangement. The optical hydrology system 700 further includes a plurality of optical fibers 724 disposed in a corresponding number of apertures 722 disposed in the first and second surfaces 712a and 712b, respectively.

In one embodiment, the system 700 includes a generator 714 that is configured to supply electrosurgical energy to patient tissue 2. An optical spectrometer 716 is operably coupled to the generator 714. The electrosurgical generator 710 is operably coupled to the hydrology array 710. In addition, a processor 730 is disposed in operative communication with the generator 714 and with the spectrometer 716. The spectrometer 720 may include a light source 732 for transmitting light to expose the tissue 2 to light; and a light detector 734. The light detector 734 is configured to sense changes in light through the tissue 2 in response to tissue treatment and communicate such changes to the processor 730 to determine tissue hydration levels.

The plurality of optical fibers 724 are operably coupled to the generator 714 and are configured to communicate light between the generator 714 and the tissue 2. In one embodiment, the spectrometer 716 is a near infra-red spectrometer providing light in the near infrared wavelength range as the light source 722. More particularly, at least one of the optical fibers 724a of the array 710 is configured to operatively communicate light 755 originating from the light source 732 to enable transmitting the light 755 towards the tissue 2. In addition, one or more of the optical fibers 724b of the array 710 is configured to receive light reflected from the tissue 2 and to transport the light 755 to the light detector 734.

The light 755, originating from the light source 732, travels in a generally U-shaped path 760 from ends 726 of the optical fibers 724a to ends 728 of optical fibers 724b and then to the light detector 734. Thus, an optic fiber distance d is defined between adjacent optical fibers 724 and particularly between ends 726 of the optical fibers 724a to ends 728 of optical fibers 724b. The optical fiber distance d is within a range of about four (4) mm to about ten (10) mm to optimize and/or enable the transmission of light 755 through the tissue 2 to determine hydration levels in the tissue 2. In one embodiment, range of the distance d extends from about three (3) mm to about twelve (12) mm. The processor 730 is configured to at least record and/or analyze changes in hydration of the tissue 2 sensed by the spectrometer 716 across the optic fiber distance d. The "banana-shaped" path of light 755 is that portion of the light emitted at the end 726 of optical fiber 724a that can be detected by the end 728 of the optical fiber 724b and does not define the limits of the light distribution within the tissue 2.

In one embodiment, the system 700 includes a temperature monitor 702. The temperature monitor 702 may be an optical temperature monitor and operatively communicates with the processor 730 and may be operably coupled to one or more fibers 724c. The temperature monitor 702 is described as an optical temperature monitor although other type of temperature monitors such as thermo-electrical or chemical or thermo-mechanical monitors may be used. The optical fiber(s) 724c is/are configured to enable the temperature monitor 702 to monitor the temperature of the light 755 reflected through the tissue 2 originating from the light source 732. End 727 of the optical fiber 724c that is configured to enable the temperature monitor 702 to monitor the temperature of the light 755 is positioned in interfacing relationship with the generally U-shaped path 760 of the light 755 that travels from the end 726 of the optical fiber 724a to end 728 of optical fiber 724b. The processor 730 is configured to record and/or analyze changes in temperature of the tissue 2 sensed by the temperature monitor 702.

In one embodiment, the system 700 may include a light source 732' that is independent of the spectrometer 716. The independent light source 732' is in optical communication with the optical fiber 724a to propagate light 755 through the optical hydrology array and with the processor 730. Additionally, a mechanical-optical multiplexer switch 740 may be included in the path of optical fiber 724b to enable the light 755 propagating through optical fiber 724b to be transferred from the light detector 734 housed in the spectrometer 716 to the independent detector 734'.

FIG. 20 is a schematic view of one embodiment of the mechanical-optical multiplexer switch 740 included within the system 700 for monitoring water displacement of FIG. 19 as configured with respect to the array of optical transmitters and optical sensors illustrated in FIG. 11.

Figure 21:
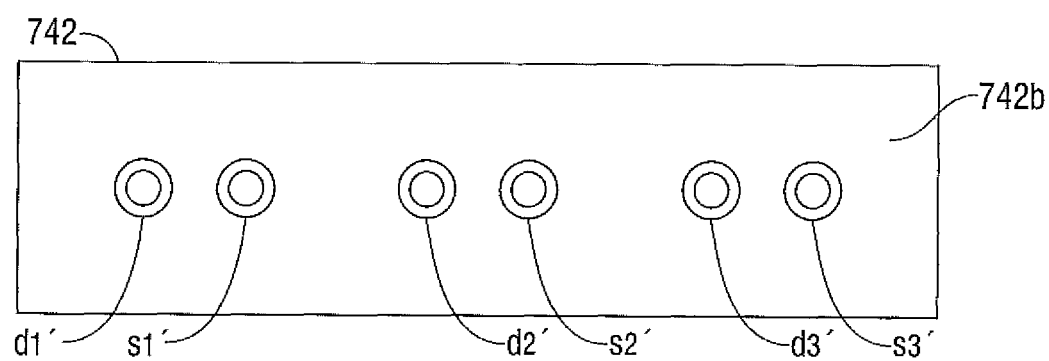
FIG. 21 is a view of an optical alignment member included within the mechanical-optical multiplexer switch taken along section line 21-21 illustrated in FIG. 20.

FIG. 21 is a view of optical alignment member 742 included within the mechanical-optical multiplexer switch 742.

The multiplexer switch 742 provides mechanical-optical alignment between one or more light sources 732, e.g., light source 7321 emitting in a wavelength range of about 200 nanometers (nm) to about 2000 nm, light source 7322 emitting in a wavelength range of about 400 nm to about 2000 nm, and light source 7323 emitting in a wavelength range of about 600 nm to about 2000 nm and patient tissue 2 (see also FIG. 19) and between patient tissue 2 and one or more light detectors, e.g., light detector 7341 detecting in a wavelength range of about 300 nm to about 900 nm and light detector 7342 detecting in a wavelength range of about 850 nm to about 2500 nm. The wavelength ranges disclosed herein represent exemplary embodiments of the present disclosure and are not intended to be limiting.

The switch 740 includes a first optical fiber alignment member 742 (an "instrument side" optical alignment member) that is configured with at least first and second surfaces 742a and 742b, respectively, on opposing sides of the alignment member 742. The first and second surfaces 742a and 742b each include a plurality of ports disposed thereupon, e.g., ports d1, s1, d2, s2, d3, s3 on first surface 742a and ports d1', s1', d2', s2', d3', s3' on second surface 742b.

Two or more corresponding ports on the first surface, e.g., ports s1, s2, s3 on first surface 742a, are configured to enable optical communication between one or more light sources, e.g., first light source 7321, second light source 7322, and third light source 7323, and the optical alignment member 742.

Additionally, two or more corresponding ports on the first surface, e.g., ports d1, d2, d3 on first surface 742a are configured to enable optical communication between the optical alignment member 742 and one or more light detectors, e.g., light detector 7341 and light detector 7342.

Two or more corresponding ports on the second surface, e.g., ports s1', s2', s3' on surface 742b, are configured to enable optical communication between two or more corresponding ports on the first surface, e.g., ports s1, s2, s3, respectively, that are configured to enable optical communication between the one or more light sources, e.g., first light source 7321, second light source 7322, and third light source 7323, and the optical alignment member 742 via corresponding channels 762 disposed therebetween, Similarly, two or more corresponding ports on the second surface, e.g., ports d1', d2', d3', are configured to enable optical communication between two or more corresponding ports on the first surface, e.g., ports d1, d2, d3, respectively, that are configured to enable optical communication between the optical alignment member 742 and at least one light detector, e.g., light detector 7341 and light detector 7342, via corresponding channels 764 disposed therebetween.

As indicated in FIG. 20, ports s1 and s1' are aligned with first light source 7321, ports s2 and s2' are aligned with second light source 7322 and ports s3 and s3' are aligned with light source 7323. Ports d1 and d1' are aligned with first light detector 7341 and ports d2 and d2' and d3 and d3' are aligned with the second light detector 7342.

The switch 740 also includes a second optical fiber alignment member 752a (a first "tissue-side" optical alignment member) configured with the first and second surfaces 754a and 754b, respectively. In a similar manner, the first and second surfaces 754a and 754b each include a plurality of ports 1d1', 1s1', 1d2', 1s2', 1d3', 1s3' and 1d1, 1s1, 1d2, 1s2, 1d3, 1s3, respectively, disposed thereupon, Two or more corresponding ports on the first surface, e.g., ports 1s1', 1s2', 1s3', are configured to enable optical communication between corresponding optical ports on the optical member 752, e.g., ports s1', s2', s3' on the surface 742b of the first optical member 742, via corresponding channels 762 disposed therebetween, Two or more corresponding ports on the second surface, e.g., ports 1d1, 1d2, 1d3, of the second optical alignment member 752 are configured to enable optical communication between corresponding optical ports 1d1', 1d2', 1d3' on the first surface 752a of the second optical alignment member 752a via corresponding channels 764 disposed therebetween and patient tissue 2.

Similarly, at least a third optical fiber alignment member, e.g., optical alignment members 752b, 752c . . . 752n (or second, third . . . nth "tissue-side" optical alignment members) are also configured with at least the first and second surfaces 754a and 754b, respectively. Again, the first and second surfaces 754a and 754b each include a plurality of ports 1 disposed thereupon, e.g., ports 2s1', 2s2', 2s3', 2d1', 2d2', 2d3' and 2s1, 2s2, 2s3, 2d1, 2d2, 2d3 on surfaces 752a and 752b of third optical alignment member 752b, ports 3s1', 3s2', 3s3', 3d1', 3d2', 3d3' and 3s1, 3s2, 3s3, 3d1, 3d2, 3d3 on surfaces 754a and 754b of fourth optical alignment member 752c, up through ports ns1', ns2', ns3', nd1', nd2', nd3' and ns1, ns2, ns3, nd1, nd2, nd3 on surfaces 754a and 754b of nth optical alignment member 752n, respectively.

In view of the foregoing description of optical alignment members 742 and 752a, optical alignment is provided via the channels 762 and 764 and aforementioned ports of the third through nth optical alignment members 752b through 754n. As defined herein, the nth optical alignment member represents at least the third optical alignment member and may include a greater number within the limits of practicality.

As illustrated in FIG. 20, the first optical alignment member 742 is movable, as indicated via the arrows "A" and "B" in a linear direction, with respect to the second and at least the third optical alignment members, e.g., 752a, 752b, 752c . . . 752n to enable the optical alignment between the light sources 7321, 7322 and 7323 and patient tissue 2 and between patient tissue 2 and the light detectors 7341 and 7342.

The optical alignment occurs when the first optical alignment member 742 has been moved to a position with respect to, for example, fourth optical alignment member 752c such that ports s1', s2', s3' on the second surface 742b of the first optical alignment member 742 are aligned with the ports 3s1', 3s2', 3s3', respectively, on the first surface 754a of the fourth optical alignment member 752c, and when the ports d1', d2', d3' on the second surface 742b of the first optical alignment member 742 are aligned with the ports 3d1', 3d2', 3d3' of the fourth optical alignment member 752c.

For clarity, optical fibers are not shown in the channels 762 and 764 or separately numbered. The result of the optical alignment is that light from first light source 7321 propagates through the optical fibers in the first optical alignment member 742 ("instrument side") to interface with the corresponding optical fibers in the fourth optical alignment member 752c ("tissue side") to form a first light path 7551 in patient tissue 2 between first light source 7321 emitting at a wavelength of about 200 nm to 2000 nm to first light detector 7341 detecting at wavelengths of about 300 nm to about 900 nm.

Similarly, light from second light source 7322 propagates through the optical fibers in the first optical alignment member 742 ("instrument side") to interface with the corresponding optical fibers in the fourth optical alignment member 752c ("tissue side") to form a second light path 7552 in patient tissue 2 between second light source 7322 emitting at a wavelength of about 400 nm to 2000 nm to second light detector 7342 detecting at wavelengths of about 850 nm to about 2500 nm.

Additionally, light from third light source 7323 propagates through the optical fibers in the first optical alignment member 742 ("instrument side") to interface with the corresponding optical fibers in the fourth optical alignment member 752c ("tissue side") to form a third light path 7553 in patient tissue 2 between third light source 7323 emitting at a wavelength of about 600 nm to 2000 nm to second light detector 7342 detecting at wavelengths of about 850 nm to about 2500 nm.

For simplicity, the same optical hydrology array 710 illustrated in FIG. 19 is positioned between the "tissue-side" optical alignment members 752a . . . 752n and the patient tissue 2. It should be noted that the same optical hydrology array 710 is associated with the differing "tissue-side" optical alignment members 752a . . . 752n. That is, different groups of the optical fibers associated with the optical hydrology array 710 are routed to and from through the array 10 and separate to be associated with corresponding "tissue-side" optical alignment members 752a . . . 752n to provide differing details of water motility information with respect to the patient tissue 2.

Although FIG. 20 is a schematic view of one embodiment of the mechanical-optical multiplexer switch 740 included within the system 700 for monitoring water displacement of FIG. 19 as configured with respect to the array of optical transmitters and optical sensors illustrated in FIG. 11, that is, the switch 740 is configured wherein one sensing (detecting) optical fiber is associated with a corresponding transmitting (source or emitting) optical fiber, system 700 may further be modified to include optical splitters (not shown) in the paths between the patient tissue 2 and the "tissue-side" optical alignment members 752a, 752b to 752n to accommodate situations where there is a mis-match in the number of transmitting or source fibers with respect to the number of sensing or detecting fibers.

Similarly, system 700 may further be modified to include optical splitters (not shown) in the paths between the "instrument side" optical alignment member 742 and the light sources 7321, 7322, 7323 and light detectors 7341, 7342 also to accommodate situations where there is a mismatch in the number of transmitting or source fibers with respect to the number of sensing or detecting fibers.

The "instrument-side" optical alignment member 742 and the "tissue-side" optical alignment members 752a . . . 752n may be configured to be substantially identical, and are illustrated as mirror images of one another. Also, the number of ports d1, s1, d2, s2, d3, s3 and d1', s1', d2', s2', d3', s3' etc. and channels 762 and 764 may be varied as necessary or advantageous. Additionally, the mechanical-optical multiplexer switch 740 may be configured wherein the second and at least a third optical alignment members 752a . . . 752n ("tissue-side" members) are movable with respect to the first optical alignment member 742 ("instrument-side" member) to enable the optical alignment between the at least one light source, e.g., light sources 7321, 7322, 7323, and patient tissue 2 and between patient tissue 2 and the at least one light detector, e.g., light detectors 7341, 7342. Although such motion would also be linear as indicated by the arrows "A" and "B", other configurations of the "tissue-side" optical alignment members 752a . . . 752n may be devised, such as wherein the optical alignment member 742 rotates around the optical alignment members 752a . . . 752b or vice versa. The embodiments are not limited with respect to the direction and type of motion of the optical alignment members.

The mechanical-optical multiplexer switch 740 has been described with respect to the electrically conductive member 300d illustrated in FIG. 11, which in FIGS. 19-20 is equivalent to the optical hydrology array 710. The mechanical-optical multiplexer switch 740 is configured for the embodiment of FIG. 11 wherein the optical fibers are routed entirely to and from the patient tissue 2 as opposed to electrically conductive member 300a illustrated in FIGS. 7 and 7A wherein light-emitting electronic devices 2561' and photoelectric detectors 2562' and 2563' and associated electrical cables 2541 and 2542 are employed.

The mechanical-optical multiplexer switch 740 may be made from an opaque material such as a metal or metal alloy, a plastic or a ceramic or suitable combinations thereof to prevent interference by light transmission between the optical fibers in the various channels 762 and 764. Dashed box 770 represents a common housing within which the processor 730, spectrometer 716, and the generator 714 may be incorporated therein. Additionally, temperature monitor 702 may be incorporated within the housing 770 or may be located elsewhere such as on or in the electrosurgical instrument. Supporting structure (not shown) for the optical alignment members 742 and 752a . . . 752n may be provided by the switch housing. Also, the motion of the optical alignment members 742 and 752a . . . 752n with respect to each other may be effected by electrical, mechanical, chemical, pneumatic or other movers suitable for the application.

In view of the previous descriptions of electrosurgical pencil blades 106a to 106d described with respect to FIGS. 1-6B, of electrically conductive members 300a to 300f and 300f' described with respect to FIGS. 7 to 13, of end effector assemblies 405a to 405e described with respect to FIGS. 14 to 15D, and of end effector assemblies 505a to 505c described with respect to FIGS. 16 to 18, the electrosurgical pencil blades 106a to 106d, the electrically conductive members 300a to 300f and 300f', the end effector assemblies 405a to 405e, and the end effector assemblies 505a to 505c may be substituted for the optical hydrology array 710 in FIG. 19 for either light reflectance or light transmission applications, as applicable to the particular blade or assembly.

Referring to FIG. 19, the near Infrared (IR) wavelength optical spectrometer 716 and optical fibers 724 sense changes across the array 710 and correlate the changes with movement of water through the tissue. Light reflected by the tissue enables detecting water content and transmitted light.

As described above with respect to FIG. 20, first light source 7321 emits light at a wavelength of about 200 nm to 2000 nm to first light detector 7341 detecting at wavelengths of about 300 nm to about 900 nm. Second light source 7322 emits light at a wavelength of about 400 nm to 2000 nm to second light detector 7342 detecting at wavelengths of about 850 nm to about 2500 nm. Additionally, third light source 7323 emits light at a wavelength of about 600 nm to 2000 nm to second light detector 7342 detecting at wavelengths of about 850 nm to about 2500 nm.

The values of the electrical, thermal and hydraulic conductivities of the tissue all depend on the quantity and location of the water content within the tissue. The analysis of the quantity and location of the water content within the tissue may be determined by comparing intensities of the light passing through the patient tissue both spatially and temporally, that is by comparing the measured intensities to the spatial location and to the time at which the measurements have been made.

First, a reference wavelength $\lambda r$ may be defined as a measured wavelength of light that is insensitive to the moisture content of the tissue. Reference wavelength $\lambda r$ is a function of x, y and t, where x and y define a two-dimensional location of the measurement within the patient tissue with respect to a reference set of x-y coordinate axes and t defines the time of the measurement. For any given tissue, there are multiple wavelengths $\lambda r$ that are insensitive to the moisture content of the tissue. The reference wavelength $\lambda r$ is then defined as follows:

$$\lambda r = f(x, y, t) \qquad \text{Eq. 1}$$

A reference intensity Ir may be defined as the intensity of light passing through patient tissue as measured at a selected particular reference wavelength $\lambda r$ that is a measured wavelength of light that is insensitive to the moisture content of the tissue. Since $\lambda r$ is a function of x, y and t, then Ir is also a function of $\lambda r$, x, y and t, as follows:

$$Ir = f[\lambda r(x, y, t)] \qquad \text{Eq. 2}$$

Reference intensity Ir is measured at a wavelength that is known not to be sensitive to the presence of water.

Next, hydration wavelength $\lambda h$ may be defined as a measured wavelength of light at which the intensity of light passing through the tissue varies depending on the moisture content of the tissue. Hydration wavelength $\lambda h$ is a function of x, y and t, where x and y define a two-dimensional location of the measurement within the patient tissue with respect to a reference set of x-y coordinate axes and t defines the time of the measurement. The hydration wavelength $\lambda h$ is then defined as follows:

$$\lambda h = f(x, y, t) \qquad \text{Eq. 3}$$

For any given tissue sample, there are a range of multiple, discrete hydration wavelengths $\lambda h$ at which the intensity of light passing through patient tissue is sensitive to the moisture content of the tissue. The particular hydration wavelength $\lambda h$ at which the intensity of the light passing through patient tissue is measured during the electrosurgical procedure may be selected as that wavelength that exhibits the greatest level of gain with respect to the moisture content of the tissue.

A hydration intensity Ih may be defined as a function of $\lambda h$, x, y and t, where $\lambda h$ defines the measured wavelength of light that is dependent on the moisture content of the tissue, x and y define a two-dimensional location of the measurement within the patient tissue with respect to a reference set of x-y coordinate axes and t defines the time of the measurement. Therefore, the hydration intensity Ih is defined as follows:

$$Ih = f[\lambda h(x, y, t)] \qquad \text{Eq. 4}$$

The intensities Ir and Ih may be measured in counts of photon emissions per unit of time. Alternatively, other units of measurement may be applied such as the candela (cd, the Standards International SI unit of measurement for light intensity) or the lumen (lm, the SI unit for measuring the flux of light being produced by a light source or received by a surface) or the lumen hour (lm h, the SI unit for a quantity of light, equal to one lumen of light flux continued for one hour). The analysis of the moisture content is performed by calculating the ratio R of the hydration intensity Ih to the reference intensity Ir as follows:

$$R = \{Ih[\lambda h(x, y, t)]/Ir[\lambda r(x, y, t)]\} \qquad \text{Eq. 5}$$

At location x1, y1 at time t1, Ir is determined as a function of $[\lambda r(x1, y1, t1)]$. Ih is determined as a function of $[\lambda h(x1, y1, t1)]$. The ratio R is then calculated:

$$R(111/111) = \{Ih[\lambda h(x1, y1, t1)]/Ir[\lambda r(x1, y1, t1)]\} \qquad \text{Eq. 6}$$

where $\lambda h(x1, y1, t1)$ is the hydration wavelength measured at location x1, y1 at time t1 and $\lambda r(x1, y1, t1)$ is the reference wavelength measured at location x1, y1 at time t1.

A subsequent measurement of the reference wavelength $\lambda r$, reference intensity Ir, hydration wavelength $\lambda h$ and hydration intensity Ih may be taken at the same location but at a different time and a new ratio of intensities calculated as follows:

$$R(112/112) = \{Ih[\lambda h(x1, y1, t2)]/Ir[\lambda r(x1, y1, t12)]\} \qquad \text{Eq. 7}$$

where $\lambda h(x1, y1, t2)$ is the hydration wavelength measured at location x1, y1 at time t2 and $\lambda r(x1, y1, t2)$ is the reference wavelength measured at location x1, y1 at time t2.

Alternatively, another measurement of the reference wavelength $\lambda r$, reference intensity Ir, hydration wavelength $\lambda h$ and hydration intensity Ih may be taken at a different location but at the same time and another ratio of intensities calculated as follows:

$$R(221/221) = \{Ih[\lambda h(x2, y2, t1)]/Ir[\lambda r(x2, y2, t1)]\} \qquad \text{Eq. 8}$$

where $\lambda h(x2, y2, t1)$ is the hydration wavelength measured at location x2, y2 at time t1 and $\lambda r(x2, y2, t1)$ is the reference wavelength measured at location x2, y2 at time t1.

Yet another measurement of the reference wavelength $\lambda r$, reference intensity Ir, hydration wavelength $\lambda h$ and hydration intensity Ih may be taken at a different location and a different time as follows:

$$R(222/222) = \{Ih[\lambda h(x2, y2, t2)]/Ir[\lambda r(x2, y2, t2)]\} \qquad \text{Eq. 9}$$

where $\lambda h(x2, y2, t2)$ is the hydration wavelength measured at location x2, y2 at time t2 and $\lambda r(x2, y2, t2)$ is the reference wavelength measured at location x2, y2 at time t2.

As can be understood from the foregoing, the ratio R may be calculated at numerous desired locations and times. The location and time of the reference wavelength $\lambda r$ and reference intensity Ir need not correspond to the location and time of the hydration wavelength $\lambda h$ and hydration intensity Ih. In such an exemplary case, the ratio R may be calculated as follows:

$$R(221/112) = \{Ih[\lambda h(x2, y2, t1)]/Ir[\lambda r(x1, y1, t12)]\} \qquad \text{Eq. 10}$$

where $\lambda h(x2, y2, t1)$ is the hydration wavelength measured at location x2, y2 at time t1 and $\lambda r(x1, y1, t2)$ is the reference wavelength measured at location x1, y1 at time t2.

The ratio R corrects for inconsistencies not related to the hydration level of the tissue. Such inconsistencies may include variation of the intensity of the light source or variations in the tissue that are not related to hydration content. The numerical values of the ratio R are dependent on the particular tissue undergoing the electrosurgical procedure and on the particular spectrometer. Wavelengths in the range of about 900 nm generally represent wavelengths at which the light intensity is generally not sensitive to hydration content and thus does not vary_with hydration content. Such wavelengths may be selected as reference wavelengths $\lambda r$. Wavelengths in the range of about 1500 nm generally represent wavelengths at which the light intensity is sensitive to hydration content, and thus do vary with hydration content. Such wavelengths may be selected as hydration wavelengths $\lambda h$.

While the measurements of the ratio R may be calculated at a fixed value of the hydration wavelength $\lambda h$ during an electrosurgical procedure, for further validation of the results, the measurements of the ratio R may be calculated at one or more other values of the hydration wavelength $\lambda h$ during the electrosurgical procedure.

A refinement of the intensity measurements may be performed to further remove spurious factors to give a more accurate reading of tissue moisture content by various mathematical operations such as addition, subtraction, multiplication and division as follows:

$$\text{Addition: } R(111/111)+R(221/221) \qquad \text{Eq. 11}$$

or $$\text{Subtraction: } R(112/112)-R(111/111) \qquad \text{Eq. 12}$$

or $$\text{Multiplication: } R(111/221)*R(212/211) \qquad \text{Eq. 13}$$

or $$\text{Division: } R(222/212)/R(221/112), \text{ etc.} \qquad \text{Eq. 14}$$

If determined to be advantageous, the above calculated ratio values of intensities may also be raised exponentially, for example, as follows:

$$\text{Multiplication: } R(111/221)^n * R(221/112)^n, \qquad \text{Eq. 15}$$

where n is a positive or negative number other than zero (and which may differ for each ratio reading such as R(111/221) or R(221/112), etc.)

The mechanical-optical multiplexer switch 740 in FIGS. 19-20 allows different wavelength intensities to be measured with respect to space and time, e.g., with respect to x-y coordinates and with respect to time t.

The array 710 provides a differential in water content and in water movement. Water movement could be in an elliptical pattern rather than a circular pattern. Based on any of the foregoing measurements, either with intensity ratio measurements alone or further refined by additional mathematical operations such as addition, subtraction, multiplication, division, etc., a Monte-Carlo analysis may be performed to determine the most probable location of the greatest moisture content within the tissue.

Movement of the mechanical-optical multiplexer switch 740 during the electrosurgical process enables acquisition of numerous intensity measurements at different locations and at different times from various locations within the array 710.

In view of the foregoing description of the optical hydrology array monitoring system 700 and electrosurgical pencil 100 and electrosurgical forceps 400, the present disclosure relates also to a method for monitoring water displacement in tissue during patient therapy. The method includes providing a spectrometer, e.g., spectrometer 716 that includes light source 732 and light detector 734. The method includes generating light 755 from the light source 732 that is reflected through the patient or subject tissue 2 and receiving the light 755 reflected through the tissue 2 wherein the light 755 reflected through the tissue 2 is received by the light detector 734.

The method may further include supplying electrosurgical energy to the tissue 2, e.g., via the electrosurgical generator 714 utilizing an energy source (not shown), sensing changes in light through the tissue 2 in response to tissue treatment, e.g. via the optical array 710, and determining changes in tissue hydration levels based on the sensed changes in light 755 through the tissue 2, e.g., via the optical spectrometer 716. The method may also include providing a processor such as the processor 730 to which the sensed changes in light 755 through the tissue 2 are communicated wherein the processor 730 determines the changes in tissue hydration levels based on the sensed changes in light 755 through the tissue 2. The processor 730 is operably coupled to the spectrometer 716 and/or the electrosurgical generator 714 and/or the energy source.

Additionally, in one embodiment, the method includes providing a plurality of optical fibers 724 arranged wherein at least one of the optical fibers 724a is configured to operatively communicate light 755 originating from the light source 732 to enable transmitting light towards the tissue 2 and at least one of the optical fibers 724b is configured to enable transporting light 755 reflected from the tissue 2.

The method may also include interfacing the one or more optical fibers 724a to the light source 732 and the one or more optical fibers 724b to the light detector 734. The method may also include configuring the plurality of optical fibers 724 in the array 710 to be separated to effect an optimal optic fiber distance d within the tissue 2, as described above.

In one embodiment, the method further includes providing light 755 in the near infrared wavelength range as the light source 732. Additionally, the method may be implemented by further including the steps of providing optical temperature monitor 702, providing one or more optical fibers 724c that operatively couple to the optical temperature monitor 702, and monitoring the temperature of light 755 reflected through the tissue 2 originating from the light source 732.

The method may be implemented wherein the one or more optical fibers 724c operatively coupled to the optical temperature monitor 702 is configured within the array 710.

In one embodiment, the method is implemented via a processor such as the processor 730 for recording and/or analyzing changes in hydration of the tissue 2 in time and/or space sensed by the spectrometer 716 based on the fiber optic distance d. Additionally, the method may be implemented wherein the processor 730 records and/or analyzes changes in temperature of the tissue 2 sensed by the optical temperature monitor 702.

Referring again to FIG. 1 and FIG. 19, the method is implemented wherein the array 710 and/or system 700 is incorporated in the electrosurgical pencil 100 including the housing 102 having proximal and distal ends 108 and 110, respectively, and the blade receptacle 105 defined at the distal end 110 of the housing 102 for supporting the electrosurgical blade 106 therein. The electrosurgical blade 106 is disposed in optical communication with the light source 732 and the light detector 734 and the method includes monitoring hydration levels in the tissue 2 during operation of the electrosurgical pencil 100.

Referring again to FIG. 14, the method is implemented wherein the arrays 710 and 710' are incorporated in the electrosurgical forceps 400 including the pair of first and second jaw members 410 and 420, respectively, disposed in pivotal relationship with respect to one another and attached to the distal end 414 of at least one shaft 412. Each jaw member 410 and 420 supports the electrically conductive surfaces 410' and 420', respectively, thereon. At least one of the jaw members 410 and/or 420 is disposed in optical communication with the light source 732, via the optical fibers 724 of the respective arrays 710 and/or 710', and the other of the jaw members 420 and/or 410, respectively being disposed in optical communication with the light detector 734, also via the optical fibers 724 of the respective arrays 710 and/or 710'. The method includes monitoring hydration levels in tissue 2 during operation of the electrosurgical forceps 400.

Again, the near Infrared (IR) wavelength optical spectrometer 716 and optical fibers 724 sense changes across the array 710 and correlate the changes with movement of water through the tissue. Light reflected by the tissue enables detecting water content and transmitted light.

Whether the optical hydrology system with the array is applied to RF therapy or to microwave therapy, the water content is a solvent. The dissolved ions travel through the solvent and their optical characteristics enable the spectrometer to sense the presence and movement of water in the tissue. The electrosurgical generator thus may be driven to control the flow of water through the tissue to optimize the delivery of energy to the tissue and thus to enhance the therapeutic effect of the particular energy treatment being applied.

As described previously, such as with respect to FIGS. 7 to 13, the array of optical fibers may be arranged in various geometries to track the motility of water through the tissue. During tissue dessication, water must be displaced to other locations within the tissue. The system array can track movement of water and then control algorithms can optimize energy induction. Again, the near Infrared (IR) wavelength optical spectrometer 716 and optical fibers 724 sense changes across the array 710 and/or 710' and correlate the changes with movement of water through the tissue. Light reflected by the tissue enables detecting water content and transmitted light.

Differences in fiber optic geometries enable detection and tracking of the manner in which water is moving through the tissue. The induction of energy can be slowly ramped up or the induction can be applied to immediately reach a steady peak value. Alternatively, the induction of energy can be applied in pulses. The energy induction process can be applied to force water out of tissue and control pulsing time and operation can be controlled to effect such forcing of water out of patient tissue.

Although the subject disclosure has been described with respect to exemplary embodiments, it will be readily apparent to those having ordinary skill in the art to which it appertains that changes and modifications may be made thereto without departing from the spirit or scope of the subject disclosure as defined by the appended claims.

What is claimed is:

1. An electrically conductive member for use with an electrosurgical instrument, the electrically conductive member comprising:
   a tissue-contacting surface configured to engage patient tissue and adapted to connect to a source of electrosurgical energy;
   a peripheral edge defined around the perimeter of the tissue-contacting surface and comprising:
   a first optical transmitter configured to propagate light into patient tissue at a reference wavelength insensitive to the moisture content of patient tissue;
   a corresponding first optical sensor configured to sense changes in light at the reference wavelength reflected from patient tissue during operation of the electrosurgical instrument;
   a second optical transmitter configured to propagate light into patient tissue at a hydration wavelength sensitive to the moisture content of patient tissue; and
   a corresponding second optical sensor configured to sense changes in light at the hydration wavelength reflected from patient tissue during operation of the electrosurgical instrument, and
   wherein at least one of the first and second optical sensors includes at least first, second and third optical fibers, each optical fiber having a diameter differing from the other two optical fibers.

2. The electrically conductive member according to claim 1, wherein the first and second optical transmitters are disposed substantially linearly relative to one another along an axis defined through the peripheral edge of the electrically conductive member from a proximal end to a distal end thereof, the first and second optical transmitters being disposed distally relative to the first and second optical sensors.

3. The electrically conductive member according to claim 1, including a first plurality of first and second optical sensors disposed in a first circumferential pattern on the peripheral edge of the electrically conductive member and a second plurality of first and second optical sensors disposed in a second circumferential pattern on the peripheral edge of the electrically conductive member concentric to the first circumferential pattern,
   wherein at least one first optical transmitter and at least one second optical transmitter are disposed substantially at the center of the concentric arrangement of the first and second circumferential patterns.

4. The electrically conductive member according to claim 1, including a first plurality of first and second optical transmitters disposed in a first circumferential pattern on the peripheral edge of the electrically conductive member and a second plurality of first and second optical transmitters disposed in a second circumferential pattern on the peripheral edge of the electrically conductive member concentric to the first circumferential pattern,
   wherein at least one first optical sensor and at least one second optical sensor are disposed substantially at the center of the concentric arrangement of the first and second circumferential patterns.

5. The electrically conductive member according to claim 1,
   wherein the first optical transmitter includes a plurality of optical fibers that form a first circumferential arrangement and the first optical sensor includes a plurality of optical fibers disposed substantially at the center of the first circumferential arrangement,
   wherein the second optical transmitter includes a plurality of optical fibers that form a second circumferential arrangement and the second optical sensor includes a plurality of optical fibers disposed substantially at the center of the second circumferential arrangement,
   wherein the second circumferential arrangement is disposed distally relative to the first circumferential arrangement.

6. The electrically conductive member according to claim 1,
   wherein the first optical sensor includes a plurality of optical fibers that form a first circumferential arrangement and the first optical transmitter includes a plurality of optical fibers disposed substantially at the center of the first circumferential arrangement,
   wherein the second optical sensor includes a plurality of optical fibers that form a second circumferential arrangement and the second optical transmitter includes a plurality of optical fibers disposed substantially at the center of the second circumferential arrangement,
   wherein the second circumferential arrangement is disposed distally relative to the first circumferential arrangement.

7. The electrically conductive member according to claim 1, wherein at least one of the first and second optical transmitters and at least one of the first and second optical sensors each include at least one optical fiber having a tapered end that forms a prism.

8. The electrically conductive member according to claim 7, wherein the at least one optical fiber of the first and second optical sensor and the at least one optical fiber of the first and second optical transmitter are positioned within the peripheral edge of the electrically conductive member to transmit and sense light propagating into and reflecting from patient tissue via the tapered ends that form a prism.

9. An electrically conductive member for use with an electrosurgical instrument, the electrically conductive member comprising:
- a tissue-contacting surface configured to engage patient tissue and adapted to connect to a source of electrosurgical energy;
- a peripheral edge defined around the perimeter of the tissue-contacting surface and comprising:
- a first optical transmitter configured to propagate light into patient tissue at a reference wavelength insensitive to the moisture content of patient tissue;
- a corresponding first optical sensor configured to sense changes in light at the reference wavelength reflected from patient tissue during operation of the electrosurgical instrument;
- a second optical transmitter configured to propagate light into patient tissue at a hydration wavelength sensitive to the moisture content of patient tissue; and
- corresponding second optical sensor configured to sense changes in light at the hydration wavelength reflected from patient tissue during operation of the electrosurgical instrument,
- wherein the first and second optical transmitters are disposed substantially linearly relative to one another along an axis defined through the peripheral edge of the electrically conductive member from a proximal end to a distal end thereof, the first and second optical transmitters being disposed distally relative to the first and second optical sensors.

10. An electrically conductive member for use with an electrosurgical instrument, the electrically conductive member comprising:
- a tissue-contacting surface configured to engage patient tissue and adapted to connect to a source of electrosurgical energy;
- a peripheral edge defined around the perimeter of the tissue-contacting surface and comprising:
- a first optical transmitter configured to propagate light into patient tissue at a reference wavelength insensitive to the moisture content of patient tissue;
- at least one corresponding first optical sensor configured to sense changes in light at the reference wavelength reflected from patient tissue during operation of the electrosurgical instrument;
- a second optical transmitter configured to propagate light into patient tissue at a hydration wavelength sensitive to the moisture content of patient tissue; and
- at least one corresponding second optical sensor configured to sense changes in light at the hydration wavelength reflected from patient tissue during operation of the electrosurgical instrument,
- wherein a first plurality of first and second optical sensors are disposed in a first circumferential pattern on the peripheral edge of the electrically conductive member and a second plurality of first and second optical sensors are disposed in a second circumferential pattern on the peripheral edge of the electrically conductive member concentric to the first circumferential pattern, and
- wherein at least one first optical transmitter and at least one second optical transmitter are disposed substantially at the center of the concentric arrangement of the first and second circumferential patterns.

11. An electrically conductive member for use with an electrosurgical instrument, the electrically conductive member comprising:
- a tissue-contacting surface configured to engage patient tissue and adapted to connect to a source of electrosurgical energy;
- a peripheral edge defined around the perimeter of the tissue-contacting surface and comprising:
- a first optical transmitter configured to propagate light into patient tissue at a reference wavelength insensitive to the moisture content of patient tissue;
- at least one corresponding first optical sensor configured to sense changes in light at the reference wavelength reflected from patient tissue during operation of the electrosurgical instrument;
- a second optical transmitter configured to propagate light into patient tissue at a hydration wavelength sensitive to the moisture content of patient tissue; and
- at least one corresponding second optical sensor configured to sense changes in light at the hydration wavelength reflected from patient tissue during operation of the electrosurgical instrument;
- a first plurality of first and second optical transmitters disposed in a first circumferential pattern on the peripheral edge of the electrically conductive member and a second plurality of first and second optical transmitters disposed in a second circumferential pattern on the peripheral edge of the electrically conductive member concentric to the first circumferential pattern,
- wherein at least one first optical sensor and at least one second optical sensor are disposed substantially at the center of the concentric arrangement of the first and second circumferential patterns.

12. An electrically conductive member for use with an electrosurgical instrument, the electrically conductive member comprising:
- a tissue-contacting surface configured to engage patient tissue and adapted to connect to a source of electrosurgical energy;
- a peripheral edge defined around the perimeter of the tissue-contacting surface and comprising:
- a first optical transmitter configured to propagate light into patient tissue at a reference wavelength insensitive to the moisture content of patient tissue;
- at least one corresponding first optical sensor configured to sense changes in light at the reference wavelength reflected from patient tissue during operation of the electrosurgical instrument;
- a second optical transmitter configured to propagate light into patient tissue at a hydration wavelength sensitive to the moisture content of patient tissue; and
- at least one corresponding second optical sensor configured to sense changes in light at the hydration wavelength reflected from patient tissue during operation of the electrosurgical instrument,
- wherein the first optical transmitter includes a plurality of optical fibers that form a first circumferential arrangement and the first optical sensor includes a plurality of optical fibers disposed substantially at the center of the first circumferential arrangement,
- wherein the second optical transmitter includes a plurality of optical fibers that form a second circumferential arrangement and the second optical sensor includes a plurality of optical fibers disposed substantially at the center of the second circumferential arrangement, and
- wherein the second circumferential arrangement is disposed distally relative to the first circumferential arrangement.

13. An electrically conductive member for use with an electrosurgical instrument, the electrically conductive member comprising:
- a tissue-contacting surface configured to engage patient tissue and adapted to connect to a source of electrosurgical energy;
- a peripheral edge defined around the perimeter of the tissue-contacting surface and comprising:
- a first optical transmitter configured to propagate light into patient tissue at a reference wavelength insensitive to the moisture content of patient tissue;
- at least one corresponding first optical sensor configured to sense changes in light at the reference wavelength reflected from patient tissue during operation of the electrosurgical instrument;
- a second optical transmitter configured to propagate light into patient tissue at a hydration wavelength sensitive to the moisture content of patient tissue; and
- at least one corresponding second optical sensor configured to sense changes in light at the hydration wavelength reflected from patient tissue during operation of the electrosurgical instrument,
- wherein the first optical sensor includes a plurality of optical fibers that form a first circumferential arrangement and the first optical transmitter includes a plurality of optical fibers disposed substantially at the center of the first circumferential arrangement,
- wherein the second optical sensor includes a plurality of optical fibers that form a second circumferential arrangement and the second optical transmitter includes a plurality of optical fibers disposed substantially at the center of the second circumferential arrangement, and
- wherein the second circumferential arrangement is disposed distally relative to the first circumferential arrangement.

* * * * *